(12) United States Patent
Thom et al.

(10) Patent No.: US 12,331,317 B2
(45) Date of Patent: Jun. 17, 2025

(54) COMPOSITIONS AND METHODS FOR INCREASING MEGAKARYOCYTE PRODUCTION

(71) Applicants: THE CHILDREN'S HOSPITAL OF PHILADELPHIA, Philadelphia, PA (US); THE TRUSTEES OF THE UNIVERSITY OF PENNSYLVANIA, Philadelphia, PA (US)

(72) Inventors: Christopher Thom, Media, PA (US); Benjamin Voight, Philadelphia, PA (US); Deborah French, Newark, DE (US)

(73) Assignees: THE CHILDREN'S HOSPITAL OF PHILADELPHIA, Philadelphia, PA (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 834 days.

(21) Appl. No.: 17/604,954

(22) PCT Filed: Apr. 29, 2020

(86) PCT No.: PCT/US2020/030402
§ 371 (c)(1),
(2) Date: Oct. 19, 2021

(87) PCT Pub. No.: WO2020/223303
PCT Pub. Date: Nov. 5, 2020

(65) Prior Publication Data
US 2022/0177843 A1  Jun. 9, 2022

Related U.S. Application Data

(60) Provisional application No. 62/839,919, filed on Apr. 29, 2019.

(51) Int. Cl.
*C12N 5/078* (2010.01)
*A61K 35/19* (2015.01)

(52) U.S. Cl.
CPC .......... *C12N 5/0644* (2013.01); *A61K 35/19* (2013.01); *C12N 2501/998* (2013.01); *C12N 2506/45* (2013.01); *C12N 2510/00* (2013.01)

(58) Field of Classification Search
CPC ... C12N 5/0644; C12N 2506/00; A61K 35/19
See application file for complete search history.

(56) References Cited

U.S. PATENT DOCUMENTS

| 9,145,450 | B2 | 9/2015 | Liu et al. | |
|---|---|---|---|---|
| 2012/0009676 | A1 | 1/2012 | Mack | |
| 2012/0238020 | A1* | 9/2012 | Mitchell | C12M 47/02 435/377 |
| 2013/0273655 | A1* | 10/2013 | Eaker | C12N 15/113 435/375 |
| 2014/0271590 | A1* | 9/2014 | Feng | A61P 7/04 435/325 |
| 2016/0312185 | A1* | 10/2016 | Real Luna | C12M 21/08 |

OTHER PUBLICATIONS

Zhu et al. MicroRNA-21 targets the tumor suppressor gene tropomyosin 1 (TPM1) *. Journal of Biological Chemistry 2007, 282;19:14328-14336. (Year: 2007).*

Zeddies (2015). Novel regulators of megakaryopoiesis: The road less traveled by. Thesis, Universiteitvan Amsterdam. Retreived from: Internet <https://pure.uva.nl/ws/files/2507182/160662_Zeddies_Thesis_complete_.pdf#page=1>. (Year: 2015).*

Ragu, et al., "The serum response factor (SRF)/megakaryocytic acute leukemia (MAL) network participates in megakaryocyte development" Leukemia (2010) 24(6):1227-30.

Moreau, et al., "Large-scale production of megakaryocytes from human pluripotent stem cells by chemically defined forward programming" Nat. Commun. (2016) 7:11208.

Gieger, et al., "New gene functions in megakaryopoiesis and platelet formation" Nature (2011) 480(7376):201-8.

Thom, et al., "Tropomyosin 1 genetically constrains in vitro hematopoiesis" BMC Biol. (2020) 18(1):52.

Soranzo, et al., "A genome-wide meta-analysis identifies 22 loci associated with eight hematological parameters in the HaemGen consortium" Nat. Genet. (2009) 41(11):1182-90.

Fehrmann, et al., "Trans-eQTLs reveal that independent genetic variants associated with a complex phenotype converge on intermediate genes, with a major role for the HLA" PLoS Genet. (2011) 7(8):e1002197.

Meiring, et al., "Co-polymers of Actin and Tropomyosin Account for a Major Fraction of the Human Actin Cytoskeleton" Curr Biol. (2018) 28(14):2331-2337.

Lambert, M.P., "Update on the inherited platelet disorders" Curr. Opin. Hematol. (2015) 22(5):460-6.

Standing, A.S.I., "Thrombocytopenia: a Defect in Actin Dynamics?" EMJ Hematol. (2017) 5(1):80-86.

Ardlie, et al., "Human genomics. The Genotype-Tissue Expression (GTEx) pilot analysis: multitissue gene regulation in humans" Science (2015) 348(6235):648-60.

Astle, et al., "The Allelic Landscape of Human Blood Cell Trait Variation and Links to Common Complex Disease" Cell (2016) 167(5):1415-1429.

Savill, et al., "Polymorphisms in the tropomyosin TPM1 short isoform promoter alter gene expression and are associated with increased risk of metabolic syndrome" Am. J. Hypertens. (2010) 23(4):399-404.

England, et al., "Tropomyosin 1: Multiple roles in the developing heart and in the formation of congenital heart defects" Journal of Molecular and Cellular Cardiology (2017) 106:1-13.

(Continued)

*Primary Examiner* — Christopher M Babic
*Assistant Examiner* — Jennifer S Spence
(74) *Attorney, Agent, or Firm* — Robert C. Netter, Jr.; Dann, Dorfman, Herrell & Skillman

(57) ABSTRACT

Improved platelet producing megakaryocytes and methods of use thereof are disclosed.

12 Claims, 13 Drawing Sheets

Specification includes a Sequence Listing.

(56) References Cited

OTHER PUBLICATIONS

Gateva, et al., "Tropomyosin Isoforms Specify Functionally Distinct Actin Filament Populations In Vitro" Curr. Biol. (2017) 27(5):705-713.

Pleines, et al., "Mutations in tropomyosin 4 underlie a rare form of human macrothrombocytopenia" J. Clin. Invest. (2017) 127(3):814-829.

* cited by examiner

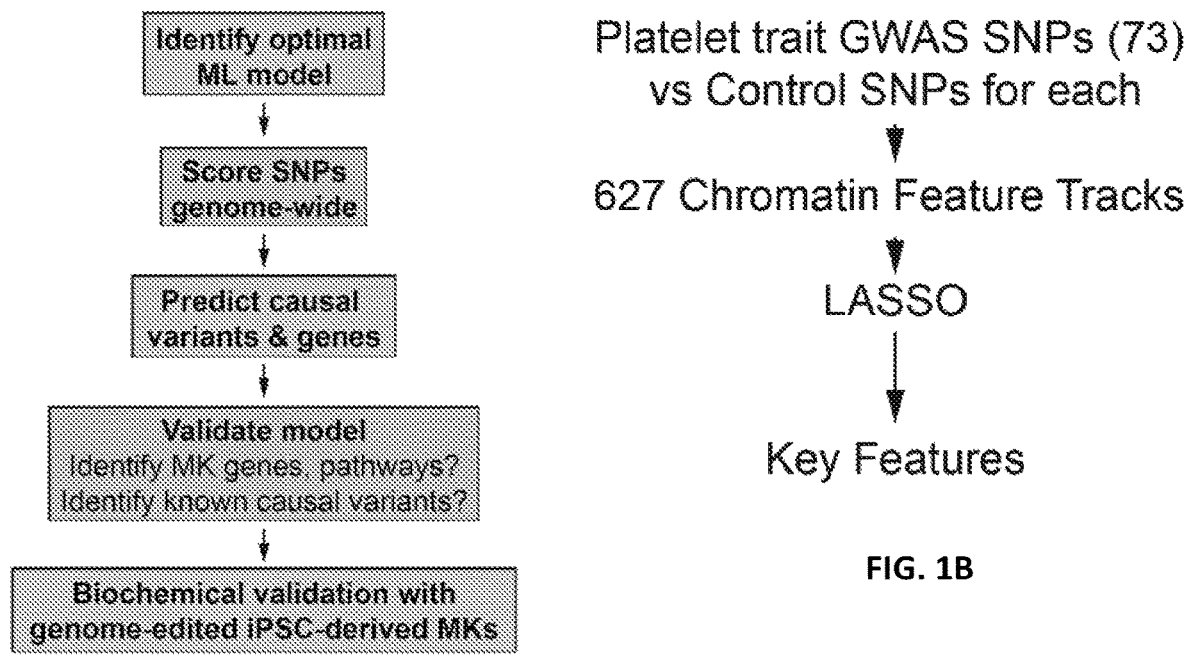
FIG. 1A
FIG. 1B
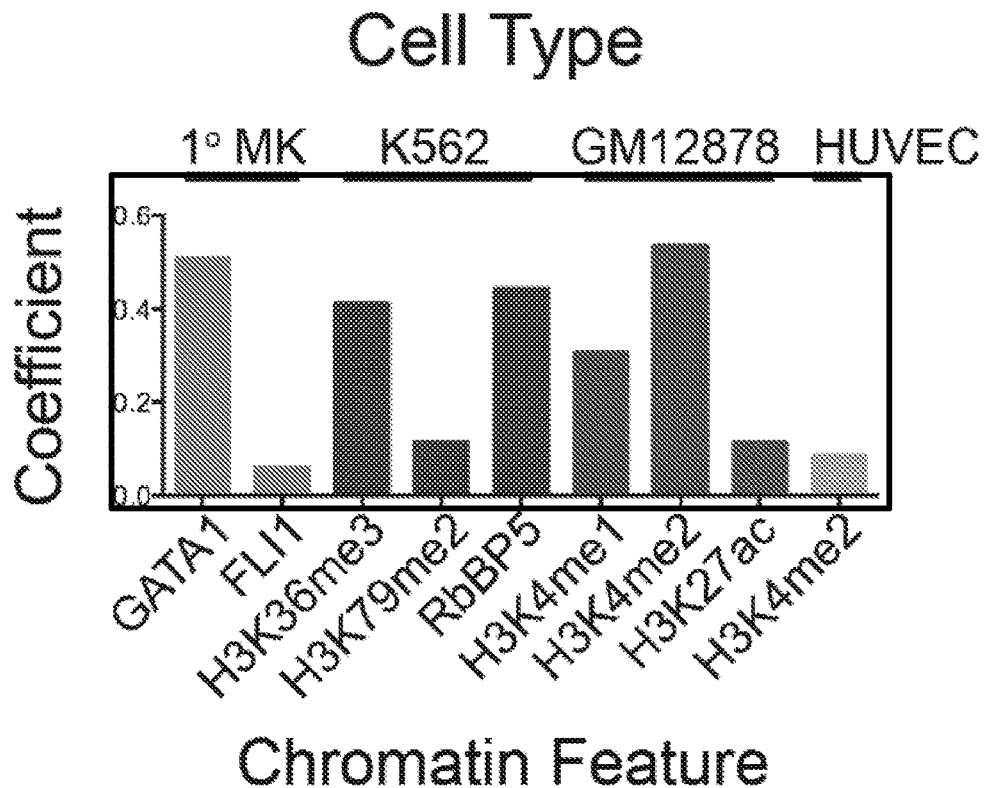
FIG. 1C

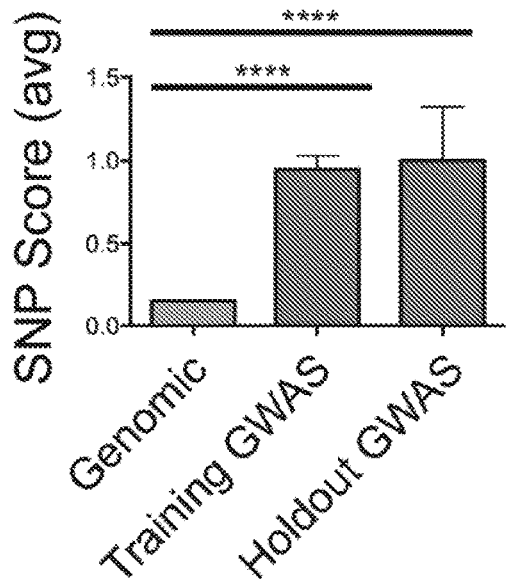
FIG. 2A
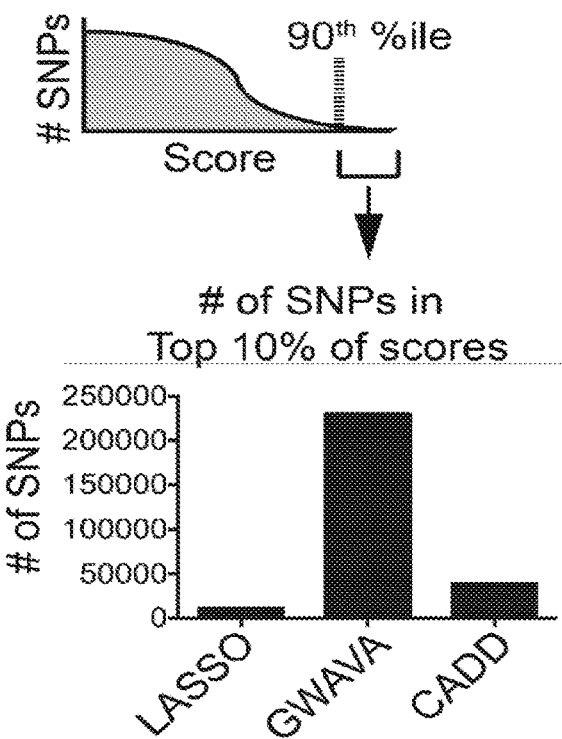
FIG. 2B
| GO Biological Process | Enrichment | Binomial p-val | FDR |
|---|---|---|---|
| LASSO | | | |
| Regulation of MK diff | + | 5.43E-05 | 4.56E-03 |
| Hemostasis | + | 9.48E-04 | 4.20E-02 |
| Platelet formation | + | 3.14E-04 | 1.80E-02 |
| Platelet morphogenesis | + | 4.11E-04 | 2.22E-02 |
| | | | |
| GWAVA | | | |
| HPC differentiation | + | 1.80E-03 | 4.73E-02 |
| Hemostasis | + | 1.70E-04 | 7.89E-03 |
| Hematopoietic or lymphoid organ development | + | 5.97E-05 | 3.41E-03 |
| Hemopoiesis | + | 1.31E-04 | 6.47E-03 |
| Platelet activation | + | 3.44E-04 | 1.38E-02 |
| | | | |
| CADD | | | |
| Regulation of hemopoiesis | - | 9.26E-05 | 1.03E-02 |
FIG. 2C rs342293
ATTATCTTGAG
..[GATA site]..

Major allele (64%)
..TTATCT..
..AATAGA..  → Normal PIK3CG

Minor allele (36%)
..TTATGT..      ↑ PIK3CG level
..AATACA..  →  ↑ MPV
                ↓ Platelet function rs11071720
TAATAGGCAA
..[GATA site]..

Major allele (51%)
..AATAG..
..TTATC..  → Normal *TPM1*

Minor allele (49%)
..AACAG..       ↓ *TPM1* level
..TTGTC..  →   ↓ MPV
                ↑ PLT#

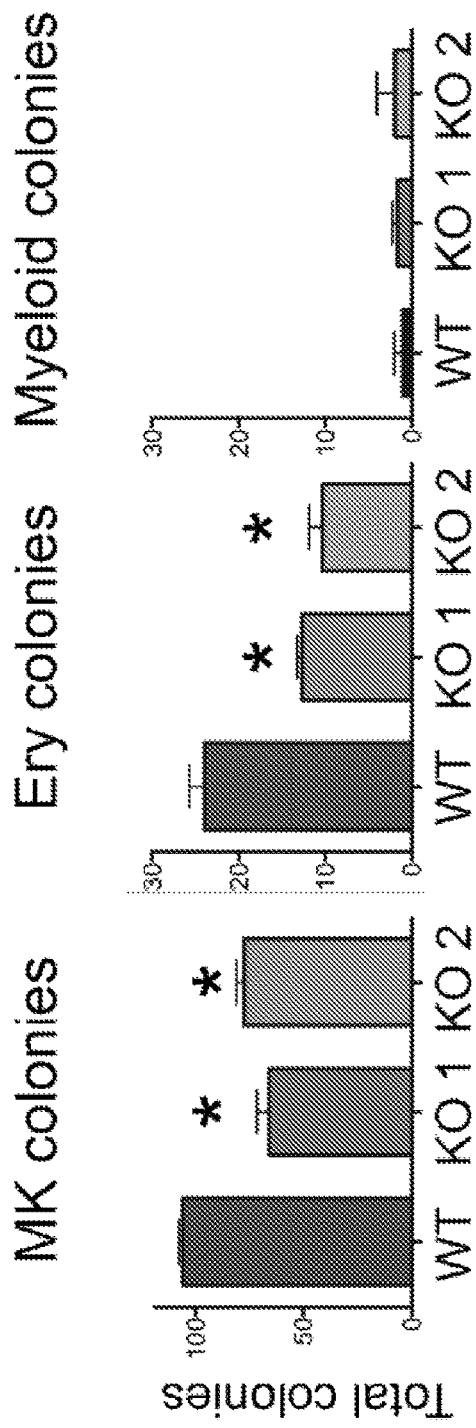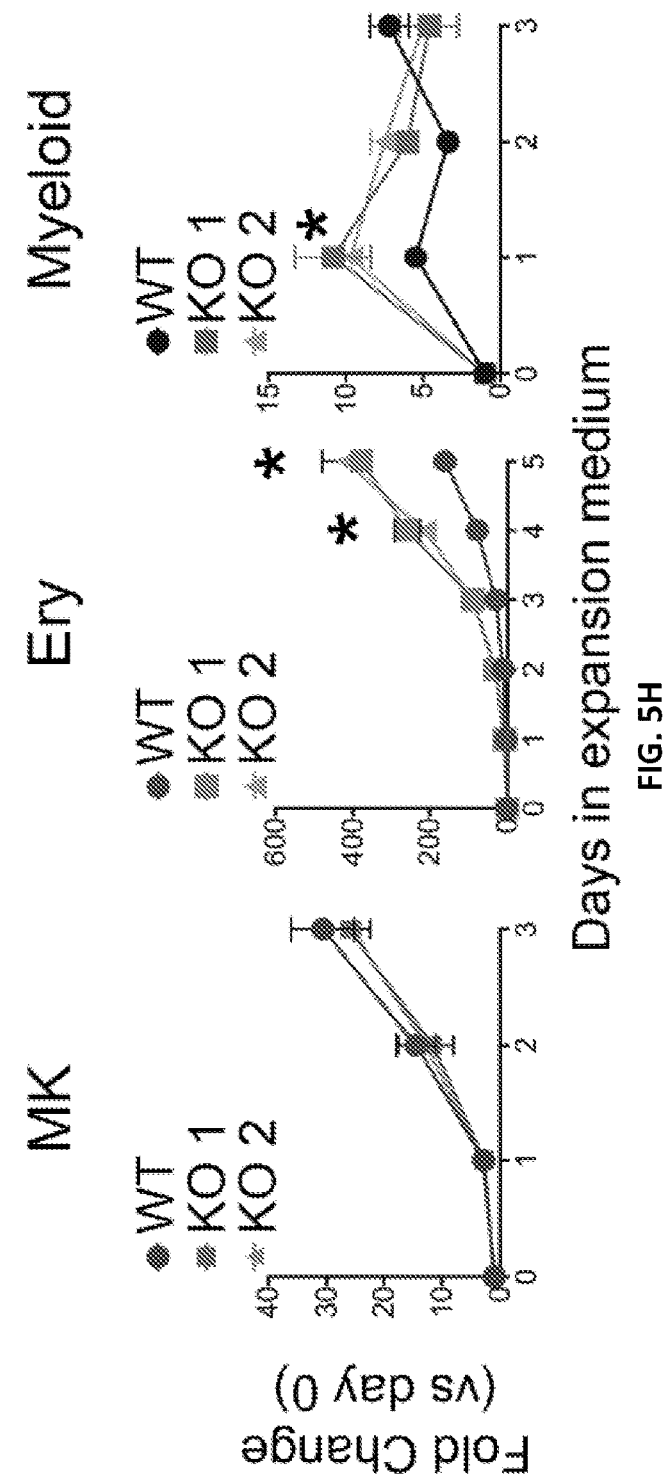
FIG. 5G
FIG. 5H

HPC precursor cell frequency

HPC yield from 300 endothelial cells

COMPOSITIONS AND METHODS FOR INCREASING MEGAKARYOCYTE PRODUCTION

This application is a § 371 application of PCT/US2020/030402, filed Apr. 29, 2020, which claims priority under 35 U.S.C. § 119 (e) to U.S. Provisional Patent Application No. 62/839,919, filed on Apr. 29, 2019. The foregoing application is incorporated by reference herein.

This invention was made with government support under Grant Nos. R01 DK101478 and T32 HD043021 awarded by the National Institutes of Health. The government has certain rights in the invention.

FIELD OF THE INVENTION

The present invention relates to the fields of medicine and hematology. More specifically, the invention provides methods for generating megakaryocytes and platelets.

BACKGROUND OF THE INVENTION

Several publications and patent documents are cited throughout the specification in order to describe the state of the art to which this invention pertains. Each of these citations is incorporated herein by reference as though set forth in full.

Platelets impact hemostasis, inflammation, wound healing and cardiovascular disease, yet mechanisms that direct megakaryocytes and platelets development and function are incompletely understood (Jurk, et al., Semin. Thromb. Hemost. (2005) 31:381-392; Daly, M. E., Blood Rev. (2017) 31:1-10). Low platelet count (thrombocytopenia) increases bleeding risk. Allogeneic donor-derived platelet transfusions mitigate bleeding risk by increasing platelet count, but are detrimental in certain vulnerable populations (e.g. preterm infants) (Curley, et al., N. Engl. J. Med. (2018) 380:242-251). Further, the supply of donated platelets cannot meet clinical demand. This has sparked interest in generating platelets from in vitro culture of induced pluripotent stem cells (Ito, et al., Cell (2018) 174:636-648). Recent advances have increased platelet yield from in vitro systems, but generating in vitro megakaryocytes cost-effectively will require better knowledge of genes and mechanisms underlying megakaryocyte development (Ito, et al., Cell (2018) 174:636-648; Noh, et al., J. Clin. Invest. (2015) 125: 2369-2374; Sim, et al., Blood (2016) 127:1227-1233). Therefore, there is an obvious need for a better understanding of megakaryocyte development and means for improving their production.

SUMMARY OF THE INVENTION

In accordance with the present invention, compositions and methods for the production of megakaryocytes and/or platelets are provided. In a particular embodiment, the method comprises contacting stem cells with a tropomyosin 1 (TPM1) inhibitor and/or inactivating the TPM1 gene, thereby producing megakaryocytes. In a particular embodiment, the stem cells are induced pluripotent stem cells. In a particular embodiment, the method further comprises contacting the stem cells with megakaryocyte differentiation inducers. In a particular embodiment, the TPM1 inhibitor is an inhibitory nucleic acid molecule such as an antisense molecule, siRNA, and/or shRNA. In a particular embodiment, the TPM1 gene is inactivated by delivering a gene editing system specific for the TPM1 gene to the cell such as CRISPR (e.g., Cas9 or a nucleic acid molecule encoding Cas9 and TPM1 gRNA). The methods may comprise isolating the produced megakaryocytes. In a particular embodiment, the method further comprises activating the megakaryocytes to produce platelets and, optionally, isolating the produced platelets.

In accordance with another aspect of the present invention, methods of treating thrombocytopenia in a subject in need thereof are provided. In a particular embodiment, the method comprises administering megakaryocytes and/or platelets produced by the method of the instant invention to the subject.

BRIEF DESCRIPTION OF THE DRAWINGS

FIGS. 1A and 1B provide a schematic of a machine learning approach to identify genes and loci that regulate megakaryocyte and platelet development. FIG. 1C provides a graph of the LASSO coefficients, indicating the relative importance of each feature, of 9 chromatin features.

FIG. 2A provides a comparison of genome-wide SNP scores (snp147), 73-GWAS SNP training set, and an 8-GWAS SNP holdout set. Bars represent mean±SEM, ****$p<0.0001$ by one-way ANOVA. FIG. 2B provides SNPs scored within the top 10% of scores genome-wide were identified (e.g., if the top score was 1.0, how many SNPs were assigned a score of 0.9 or greater) and quantified the bar plot. FIG. 2C provides the biological processes of the top 4000 highest-scoring SNPs for LASSO, GWAVA, or CADD, as analyzed by Gene Ontology. Hematopoietic pathways identified with a false discovery rate (FDR)<25% are shown. Positive (+) or negative (−) pathway enrichment is noted.

showing loss of TPM1 protein KO clones.

FIG. 5G shows single cells (typically HPCs) from differentiation day 8 that were put into megacult (megakaryocyte) or methylcellulose (ery, myeloid) to perform colony assays. After 2 weeks, colonies were counted. Bars represent total colonies counted (mean±SD) for 3-4 replicates for each clone. FIG. 5H shows progenitors from differentiation day 8 that were put into lineage expansion medium containing thrombopoietin (megakaryocyte), erythropoietin (Ery), or G-CSF (myeloid). Cells were analyzed by counting and FACS for 3-5 days. Lines represent number of lineage-specific cells multiplied by total cell count on each day, normalized to cell count on day of plating (day 0). Mature lineage-specific cells were CD41$^+$/CD42b$^+$ (MK), CD235$^+$/CD41$^-$ (Ery) or CD45$^+$ (myeloid). *p<0.05.

DETAILED DESCRIPTION OF THE INVENTION

Figures 3A, 3B, 3C:
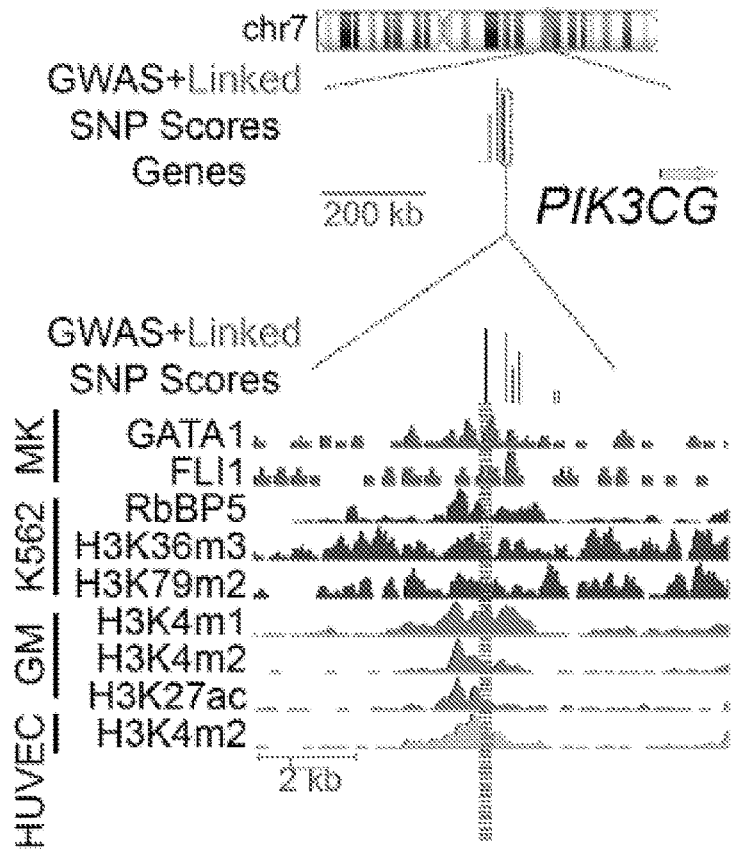
FIG. 3A shows a chromosome 7 ideogram, SNP scores and location of the PIK3CG gene near platelet trait GWAS SNP rs342293. The GWAS SNP is shown in black and linked SNPs ($r^2>0.8$) are shown, with bar heights corresponding to SNP scores. The boxed region is expanded to show genomic context, including key chromatin features identified by the LASSO model, which contribute to SNP scores. Cell types and chromatin feature labels are shown at left.
FIG. 3B shows the local DNA sequence, including the rs342293 SNP (underlined) and a canonical GATA binding site. Provided sequence is SEQ ID NO: 8.
FIG. 3C shows the major and minor rs342293 alleles and associated phenotypes.

Allogeneic platelet transfusions can treat thrombocytopenia, but an inadequate supply of donor-derived platelets has sparked interest in generating transfusable platelets in vitro. In particular, better understanding genetic mechanisms that augment megakaryocyte yield will increase the cost-effectiveness of in vitro cultures. Genome-wide association studies (GWAS) have linked hundreds of single nucleotide polymorphisms (SNPs) with platelet trait variation. Herein, a machine learning-based scoring algorithm was created, based on chromatin feature overlap with platelet trait GWAS SNPs, to quantitatively assess loci genome-wide. High-scoring SNPs marked relevant loci and genes, including an expression quantitative trait locus for tropomyosin 1 (TPM1). TPM1-deficient human iPSCs accelerated megakaryocyte progenitor development, identifying a novel strategy to augment in vitro megakaryocyte production.

In accordance with the present invention, methods for producing megakaryocytes are provided. In a particular embodiment, the method comprises contacting a cell with a TPM1 inhibitor, thereby driving megakaryocyte production or differentiation. In a particular embodiment, the megakaryocyte is primitive or definitive, particularly definitive. In a particular embodiment, the method comprises contacting a stem cell such as a pluripotent stem cell, induced pluripotent stem cell (iPSC), hemogenic endothelia, and/or hematopoietic stem cell (e.g., CD34$^+$), with a TPM1 inhibitor. In a particular embodiment, the method comprises contacting pluripotent stem cells or iPSCs, particularly iPSCs, with a TPM1 inhibitor. In a particular embodiment, the method further comprises contacting the cells with a modulator (e.g., activator or inhibitor) of a gene set forth in Table 2. In a particular embodiment, the cells being contacted with a TPM1 inhibitor are autologous to a subject to be treated with the produced megakaryocytes and/or platelets. The methods may further comprise contacting the stem cells with inducers for megakaryocyte differentiation. Examples of inducers for megakaryocyte differentiation include, without limitation, vascular endothelial growth factor (VEGF), stem cell factor (SCF), thrombopoietin (TPO), and/or interleukin-3 (IL-3). The methods may further comprise inducing the megakaryocytes to produce platelets. In a particular embodiment, the megakaryocytes are contacted with thrombin, convulxin, and/or adenosine diphosphate (ADP). In a particular embodiment, the megakaryocytes may be induced to produce platelets in vitro. For example, the megakaryocytes may be infused into a platelet bioreactor, wherein the megakaryocytes release functional platelets into the bioreactor environment (e.g., Thon et al., Platelets (2017) 28(5): 472-477; Sugimoto et al., J. Thromb. Haemost. (2017) 15(9):1717-1727; Shepherd et al., Biomaterials (2018) 182: 135-144; Strassel, et al., Front Med (2018) 5:239). In another embodiment, the megakaryocytes may be administered or infused into a subject, wherein the megakaryocytes release platelets in vivo.

In accordance with another aspect of the instant invention, compositions and methods for inhibiting (e.g., reducing or slowing), treating, and/or preventing a thrombocytopenia in a subject are provided. In a particular embodiment, the method comprises administering the megakaryocytes and/or platelets produced by the methods described herein to the subject. In a particular embodiment, autologous cells were used in the megakaryocyte and/or platelet production methods. In a particular embodiment, the methods comprise administering to a subject in need thereof a therapeutically effective amount of at least one TPM1 inhibitor (e.g., to stem cells or hematopoietic stem cells (e.g., bone marrow) in the subject). The TPM1 inhibitor may be administered in a composition further comprising at least one pharmaceutically acceptable carrier.

The above methods also encompass ex vivo methods. For example, the methods of the instant invention can comprise isolating cells (e.g., pluripotent stem cells or hematopoietic stem cell) from a subject, delivering at least one TPM1 inhibitor to the cells, and administering the treated cells to the subject. The cells may also be treated with other reagents in vitro, such as at least one inducer for megakaryocyte differentiation, prior to administration to the subject. In a particular embodiment, the megakaryocytes are induced (e.g., with thrombin or convulxin) to produce platelets, which are then administered to the subject.

TPM1 inhibitors are compounds which reduce TPM1 activity, inhibit or reduce TPM1-substrate interaction, inhibit or reduce TPM1 dimerization, and/or the expression of TPM1. In a particular embodiment, the TPM1 inhibitor is specific to TPM1 (e.g., predominantly inhibits TPM1 over other tropomyosins). Examples of TPM1 inhibitors include, without limitation, proteins, polypeptides, peptides, antibodies, small molecules, and nucleic acid molecules. In a particular embodiment, the TPM1 inhibitor is an antibody immunologically specific for TPM1. In another embodiment, the TPM1 inhibitor is an inhibitory nucleic acid molecule, such as an antisense, siRNA, or shRNA molecule (or a nucleic acid molecule encoding the inhibitory nucleic acid molecule). In a particular embodiment, the TPM1 inhibitor is a gene editing inhibitor such as a CRISPR based targeting of the TPM1 gene (e.g., with a guide RNA targeting the TPM1 gene). The TPM1 inhibitor may be a synthetic or non-natural compound.

Examples of nucleotide and amino acid sequences for human tropomyosin 1 (TPM1) are provided in GenBank Gene ID: 7168, including all variants and isoforms described therein. In a particular embodiment, the TPM1 is human. In a particular embodiment, the nucleotide and amino acid sequences are provided in GenBank Accession No. NG 007557, GenBank Accession No. NP 001018004.1 (isoforms TPM1.6cy), GenBank Accession No. NP 001018006.1 (isoform TPM1.7cy), GenBank Accession No. NP_001288218.1 (isoform TPM1.8cy), GenBank Accession No. NP 001317273.1 (isoform TPM1.9cy), GenBank Accession No. NP 001018005.1 (isoform TPM1.1st) or GenBank Accession No. NP 001018008.1 (isoform TPM1.12br). In a particular embodiment, the amino acid sequence of TPM1 is:

```
                                            (SEQ ID NO: 1)
MDAIKKKMQM LKLDKENALD RAEQAEADKK AAEDRSKQLE

DELVSLQKKL KGTEDELDKY SEALKDAQEK LELAEKKATD
```

```
-continued
AEADVASLNR RIQLVEEELD RAQERLATAL QKLEEAEKAA

DESERGMKVI ESRAQKDEEK MEIQEIQLKE AKHIAEDADR

KYEEVARKLV IIESDLERAE ERAELSEGKC AELEEELKTV

TNNLKSLEAQ AEKYSQKEDR YEEEIKVLSD KLKEAETRAE

FAERSVTKLE KSIDDLEDEL YAQKLKYKAI SEELDHALND

MTSI,
``` as provided in GenBank Accession No. NP 001018005.1. In a particular embodiment, the nucleotide sequence of TPM1 is:

```
                                            (SEQ ID NO: 2)
atggacgcc  atcaagaaga  agatgcagat  gctgaagctc gacaaggaga acgccttgga tcgagctgag caggcggagg ccgacaagaa ggcggcggaa gacaggagca agcagctgga agatgagctg gtgtcactgc aaaagaaact caagggcacc gaagatgaac tggacaaata ctctgaggct ctcaaagatg cccaggagaa gctggagctg gcagagaaaa aggccaccga tgctgaagcc gacgtagctt ctctgaacag acgcatccag ctggttgagg aagagttgga tcgtgcccag gagcgtctgg caacagcttt gcagaagctg gaggaagctg agaaggcagc agatgagagt gagagaggca tgaaagtcat tgagagtcga gcccaaaaag atgaagaaaa aatggaaatt caggagatcc aactgaaaga ggccaagcac attgctgaag atgccgaccg caaatatgaa gaggtggccc gtaagctggt catcattgag agcgacctgg aacgtgcaga ggagcgggct gagctctcag aaggcaaatg tgccgagctt gaagaagaat tgaaaactgt gacgaacaac ttgaagtcac tggaggctca ggctgagaag tactcgcaga aggaagacag atatgaggaa gagatcaagg tcctttccga caagctgaag gaggctgaga ctcgggctga gtttgcggag aggtcagtaa ctaaattgga gaaaagcatt gatgacttag aagacgagct gtacgctcag aaactgaagt acaaagccat cagcgaggag ctggaccacg ctctcaacga tatgacttcc atataa,
``` as provided in GenBank Accession No. NM_001018005. In a particular embodiment, the TPM1 has at least 90%, 95%, 97%, 99%, or 100% identity, particularly at least 97%, or 99% identity, with one of the provided sequences.

As stated hereinabove, the genome of the cell may be edited to inactivate/inhibit TPM1. The genome of the cells can be edited using any method known in the art such as, without limitation: zinc finger nucleases (ZFNs), transcription activator like effector nucleases (TALENs), and clustered regularly interspaced short palindromic repeats (CRISPRs). In a particular embodiment, CRISPR is utilized. Clustered, regularly interspaced, short palindromic repeat (CRISPR)/Cas9 (e.g., from *Streptococcus pyogenes*) technology and gene editing are well known in the art (see, e.g., Shi et al. (2015) Nat. Biotechnol., 33(6):661-7; Sander et al.

(2014) Nature Biotech., 32:347-355; Jinek et al. (2012) Science, 337:816-821; Cong et al. (2013) Science 339:819-823; Ran et al. (2013) Nature Protocols 8:2281-2308; Mali et al. (2013) Science 339:823-826; Sapranauskas et al. (2011) Nucleic Acids Res. 39:9275-9282; Nishimasu et al. (2014) Cell 156(5):935-49; Swarts et al. (2012) PLoS One, 7:e35888; Sternberg et al. (2014) Nature 507(7490):62-7; addgene.org/crispr/guide). The RNA-guided CRISPR/Cas9 system involves expressing Cas9 along with a guide RNA molecule (gRNA). Guidelines and computer-assisted methods for generating gRNAs are available (see, e.g, CRISPR Design Tool (crispr.mit.edu); Hsu et al. (2013) Nat. Biotechnol. 31:827-832; addgene.org/CRISPR; and CRISPR gRNA Design tool—DNA2.0 (dna20.com/eCommerce/startCas9)). When coexpressed, gRNAs bind and recruit Cas9 to a specific genomic target sequence where it mediates a double strand DNA (dsDNA) break. The double strand break can be repaired by non-homologous end joining (NHEJ) pathway yielding an insertion and/or deletion or, in the presence of a donor template, by homology-directed repair (HDR) pathway for replacement mutations (Overballe-Petersen et al. (2013) Proc. Natl. Acad. Sci. U.S.A. 110:19860-19865; Gong et al. (2005) Nat. Struct. Mol. Biol. 12:304-312).

The binding specificity of the CRISPR/Cas9 complex depends on two different elements. First, the binding complementarity between the targeted genomic DNA (genDNA) sequence and the complementary recognition sequence of the gRNA (e.g., ~18-22 nucleotides, particularly about 20 nucleotides). Second, the presence of a protospacer-adjacent motif (PAM) juxtaposed to the genDNA/gRNA complementary region (Jinek et al. (2012) Science 337:816-821; Hsu et al. (2013) Nat. Biotech., 31:827-832; Sternberg et al. (2014) Nature 507:62-67). The PAM motif for *S. pyogenes* Cas9 has been fully characterized, and is NGG or NAG (Jinek et al. (2012) Science 337:816-821; Hsu et al. (2013) Nat. Biotech., 31:827-832). Other PAMs of other Cas9 are also known (see, e.g., addgene.org/crispr/guide/#pam-table). Typically, the PAM sequence is 3' of the DNA target sequence in the genomic sequence.

In a particular embodiment, the method comprises administering at least one Cas9 (e.g., the protein and/or a nucleic acid molecule encoding Cas9) and at least one gRNA (e.g., a nucleic acid molecule encoding the gRNA) to the cell or subject. In a particular embodiment, the Cas9 is *S. pyogenes* Cas9. In a particular embodiment, the targeted PAM is in the 5'UTR, 3'UTR, promoter, or intron (e.g., first intron). The nucleic acids of the instant invention may be administered consecutively (before or after) and/or at the same time (concurrently). The nucleic acid molecules may be administered in the same composition or in separate compositions. In a particular embodiment, the nucleic acid molecules are delivered in a single vector (e.g., a viral vector).

In a particular embodiment, the nucleic acid molecules of the instant invention are delivered (e.g., via infection, transfection, electroporation, etc.) and expressed in cells via a vector (e.g., a plasmid), particularly a viral vector. The expression vectors of the instant invention may employ a strong promoter, a constitutive promoter, and/or a regulated promoter. In a particular embodiment, the nucleic acid molecules are expressed transiently. Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). Examples of expression vectors for expressing the molecules of the invention include, without limitation, plasmids and viral vectors (e.g., adeno-associated viruses (AAVs), adenoviruses, retroviruses, and lentiviruses).

In a particular embodiment, the guide RNA of the instant invention may comprise separate nucleic acid molecules. For example, one RNA may specifically hybridize to a target sequence (crRNA) and another RNA (trans-activating crRNA (tracrRNA)) specifically hybridizes with the crRNA. In a particular embodiment, the guide RNA is a single molecule (sgRNA) which comprises a sequence which specifically hybridizes with a target sequence (crRNA; complementary sequence) and a sequence recognized by Cas9 (e.g., a tracrRNA sequence; scaffold sequence). Examples of gRNA scaffold sequences are well known in the art (e.g., 5'-GUUUUAGAGC UAGAAAUAGC AAGUUAAAAU AAGGCUAGUC CGUUAUCAAC UUGAAAAGU GGCACCGAGU CGGUGCUUUU (SEQ ID NO: 3)). As used herein, the term "specifically hybridizes" does not mean that the nucleic acid molecule needs to be 100% complementary to the target sequence. Rather, the sequence may be at least 80%, 85%, 90%, 95%, 97%, 99%, or 100% complementary to the target sequences (e.g., the complementary between the gRNA and the genomic DNA). The greater the complementarity reduces the likelihood of undesired cleavage events at other sites of the genome. In a particular embodiment, the region of complementarity (e.g., between a guide RNA and a target sequence) is at least about 10, at least about 12, at least about 15, at least about 17, at least about 20, at least about 25, at least about 30, at least about 35, or more nucleotides. In a particular embodiment, the region of complementarity (e.g., between a guide RNA and a target sequence) is about 15 to about 25 nucleotides, about 15 to about 23 nucleotides, about 16 to about 23 nucleotides, about 17 to about 21 nucleotides, about 18 to about 22 nucleotides, or about 20 nucleotides. In a particular embodiment, the guide RNA targets a sequence or comprises a sequence (inclusive of RNA version of DNA molecules) as set forth in the Example provided herein. In a particular embodiment, the guide RNA targets a sequence or comprises a sequence (e.g., RNA version) which has at least 80%, 85%, 90%, 95%, 97%, 99%, or 100% homology or identity to a sequence set forth in the Example (e.g., SEQ ID NOs: 4-7). The sequences may be extended or shortened by 1, 2, 3, 4, or 5 nucleotides at the end of the sequence opposite from the PAM (e.g., at the 5' end). When the sequence is extended the added nucleotides should correspond to the genomic sequence.

The methods of the instant invention may further comprise monitoring the disease or disorder in the subject after administration of the composition(s) of the instant invention to monitor the efficacy of the method. For example, the subject may be monitored for characteristics of low platelet counts or thrombocytopenia.

When an inhibitory nucleic acid molecule (e.g., an shRNA, siRNA, or antisense) is delivered to a cell or subject, the inhibitory nucleic acid molecule may be administered directly or an expression vector may be used. In a particular embodiment, the inhibitory nucleic acid molecules are delivered (e.g., via infection, transfection, electroporation, etc.) and expressed in cells via a vector (e.g., a plasmid), particularly a viral vector. The expression vectors of the instant invention may employ a strong promoter, a constitutive promoter, and/or a regulated promoter. In a particular embodiment, the inhibitory nucleic acid molecules are expressed transiently. In a particular embodiment, the promoter is cell-type specific (e.g., erythroid cells). Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). Examples of expression vectors for expressing the molecules of the invention include, without limitation, plasmids and viral vectors (e.g., adeno-associated viruses (AAVs), adenoviruses, retroviruses, and lentiviruses).

Compositions comprising at least one TPM1 inhibitor and at least one carrier (e.g., a pharmaceutically acceptable carrier) are also encompassed by the instant invention. Compositions comprising megakaryocytes and/or platelets produced by the methods of the instant invention and at least one carrier (e.g., a pharmaceutically acceptable carrier) are also encompassed by the instant invention. Except insofar as any conventional carrier is incompatible with the variant to be administered, its use in the pharmaceutical composition is contemplated. In a particular embodiment, the carrier is a pharmaceutically acceptable carrier for intravenous administration.

As explained hereinabove, the compositions of the instant invention are useful for increasing hemoglobin production and for treating hemoglobinopathies and thalassemias. A therapeutically effective amount of the composition may be administered to a subject in need thereof. The dosages, methods, and times of administration are readily determinable by persons skilled in the art, given the teachings provided herein.

The components as described herein will generally be administered to a patient as a pharmaceutical preparation. The term "patient" or "subject" as used herein refers to human or animal subjects. The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The compositions of the present invention can be administered by any suitable route, for example, by injection (e.g., for local (direct) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered directly to the blood stream (e.g., intravenously). In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, PA Lippincott Williams & Wilkins. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, in which case appropriate liquid carriers, suspending agents and the like may be employed. Pharmaceutical preparations for injection are known in the art. If injection is selected as a method for administering the therapy, steps should be taken to ensure that sufficient amounts of the molecules reach their target cells to exert a biological effect.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard therapies.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient suffering from an injury, including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury, resulting in a decrease in the probability that the subject will develop conditions associated with the hemoglobinopathy or thalassemia.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated with a hemoglobinopathy or thalassemia.

As used herein, the term "subject" refers to an animal, particularly a mammal, particularly a human.

The term "vector" refers to a carrier nucleic acid molecule (e.g., RNA or DNA) into which a nucleic acid sequence can be inserted, e.g., for introduction into a host cell where it may be expressed and/or replicated. An "expression vector" is a specialized vector that contains a gene or nucleic acid sequence with the necessary operably linked regulatory regions needed for expression in a host cell. The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, amino acids, or nucleic acids.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions/fragment (e.g., antigen binding portion/fragment) of an immunoglobulin molecule, and fusions of immunologically active portions of an immunoglobulin molecule. Antibody fragments include, without limitation, immunoglobulin fragments including, without limitation: single domain (Dab; e.g., single variable light or heavy chain domain), Fab, Fab', $F(ab')_2$, and F(v); and fusions (e.g., via a linker) of these immunoglobulin fragments including, without limitation: scFv, $scFv_2$, scFv-Fc, minibody, diabody, triabody, and tetrabody.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al., Current Protocols in Molecular Biology, John Wiley and Sons, Inc). Short hairpin RNA molecules (shRNA) typically consist of short complementary sequences (e.g., an siRNA) separated by a small loop sequence (e.g., 6-15 nucleotides, particularly 7-10 nucleotides) wherein one of the sequences is complimentary to the gene target. shRNA molecules are typically processed into an siRNA within the cell by endonucleases. Exemplary modifications to siRNA molecules are provided in U.S. Application Publication No. 20050032733. For example, siRNA and shRNA molecules may be modified with nuclease resistant modifications (e.g., phosphorothioates, locked nucleic acids (LNA), 2'-O-methyl modifications, or morpholino linkages). Expression vectors for the expression of siRNA or shRNA molecules may employ a strong promoter which may be constitutive or regulated. Such promoters are well known in the art and include, but are not limited to, RNA polymerase II promoters, the T7 RNA polymerase promoter, and the RNA polymerase III promoters U6 and H1.

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods. Antisense oligonucleotides may be modified as described above to comprise nuclease resistant modifications.

The following example is provided to illustrate various embodiments of the present invention. The example is illustrative and not intended to limit the invention in any way.

EXAMPLE

Genome wide association studies (GWAS) have linked hundreds of single nucleotide polymorphisms (SNPs) with platelet trait variability (Gieger, et al., Nature (2011) 480: 201-208; Soranzo, et al., Nat. Genet. (2009) 41:1182-1190; Astle, et al., Cell (2016) 167:1415-1429; Meisinger, et al., Am. J. Hum. Genet. (2009) 84:66-71). Most GWAS SNPs are noncoding, likely influencing transcriptional expression of key genes (Hindorff, et al., Proc. Natl. Acad. Sci. (2009) 106:9362-9367; Tak, et al., Epigenetics Chromatin (2015) 8:57). It is challenging to derive functional biochemical understanding from GWAS findings (Tak, et al., Epigenetics Chromatin (2015) 8:57; Edwards, et al., Am. J. Hum. Genet. (2013) 93:779-97; Xu, et al., Nucleic Acids Res. (2009) 37:600-605) and few studies have elucidated biochemical mechanisms for platelet trait variability loci (Simon, et al., Am. J. Hum. Genet. (2016) 98:883-897; Soranzo, et al., Blood (2009) 113:3831-3837; Polfus, et al., Am. J. Hum. Genet. (2016) 99:481-488; Nurnberg, et al., Blood (2012) 120:4859-4868; Pleines, et al., J. Clin. Invest. (2017) 127: 814-829). Herein, putatively active genomic loci were computationally identified and related genes and mechanisms were validated using cellular studies (FIG. 1A).

Fundamental problems affecting GWAS validation include transparency feature selection and specificity in locus identification. Several computational methods relate genomic context to biological function (Kircher, et al., Nat. Genet. (2014) 46:310-315; Ritchie, et al., Nat. Methods (2014) 11:294-296; Zhou, et al., Nat. Methods (2015) 12:931-934), but these typically identify generic regulatory elements and are likely to underappreciate trait-specific regulatory loci. Therefore, a model was sought that prioritized megakaryocyte- and platelet-related specificity without compromising prediction sensitivity. These priorities led to consideration of penalized regression modeling using the least absolute shrinkage and selection operator (LASSO) (Tibshirani, R., J. R. Stat. Soc. B (1996) 58:267-288; Zou, et al., J. R. Stat. Soc. Ser. B Stat. Methodol. (2005) 67:301-320). LASSO allows for regularization and independent variable selection, and uses 10-fold cross-validation to avoid overfitting a data set. Transparency in feature selection had the added benefit of being able to confirm biologic validity and intuition associated with those features. LASSO was used to leverage publicly available genome-wide data from ENCODE (Feingold, et al., Science (2004) 306:636-40), ChromHMM (Ernst, et al., Nat Methods (2012) 9:215-6), and megakaryocyte-specific data sets (Tijssen, et al., Dev. Cell (2011) 20:597-609; Paul, et al., Genome Res. (2013) 23:1130-1141), generating a simple predictive model based on 9 epigenetic features that outperformed other machine learning-based predictors in its ability to discriminate platelet trait GWAS SNPs from controls. When applied genome-wide, the model highlighted SNPs known to impact megakaryocyte and platelet biology.

This LASSO-based model also identified novel putatively active loci, including SNPs within the Tropomyosin 1 (TPM1) gene locus. TPM1 regulates actomyosin contacts and cytoskeletal integrity (Gunning, et al., Curr. Biol. (2017) 27:R8-R13; Gunning, et al., J. Cell Sci. (2015) 128:2965-2974), with key roles in cardiac, neural, and cancer biology (England, et al., J. Mol. Cell. Cardiol. (2017) 106:1-13; Mckeown, et al., Dev. Dyn. (2014) 243:800-817; Thierfelder, et al., Cell (1994) 77:701-712; Watkins, et al., N. Engl. J. Med. (1995) 332:1058-1065; Olson, et al., J. Mol. Cell. Cardiol. (2001) 33:723-732; Probst, et al., Circ. Cardiovasc. Genet. (2011) 4:367-374; Brettle, et al., Brain Research Bulletin (2016) 126:311-323; Zhu, et al., Cell Res. (2008) 18:350-359; Du, et al., Oncol. Rep. (2015) 33:2807-2814). Most cellular actin is bound by various isoforms of TPM1-4 and actin cytoskeletal dynamics play critical roles in megakaryocyte and platelet development (Meiring, et al., Curr. Biol. (2018) 28:2331-2337; Lambert, et al., Curr. Opin. Hematol. (2015) 22:460-466; Standing, A. S. I., EMJ Hematol. (2017) 5:80-86). GWAS have linked SNPs near TPM1 and TPM4 with platelet trait variation (Gieger, et al., Nature (2011) 480:201-208; Soranzo, et al., Nat. Genet. (2009) 41:1182-1190; Fehrmann et al., PLoS Genet. (2011) 7(8):e1002197) and TPM4 deficiency causes macrothrombocytopenia (Pleines, et al., J. Clin. Invest. (2017) 127:814-829). Zebrafish studies show that tpma (a TPM homologue) knockdown impairs thrombopoiesis (Gieger, et al., Nature (2011) 480:201-208). Notably, TPM1 studies in mouse have been precluded by lethal cardiac dysmorphology (Mckeown, et al., Dev. Dyn. (2014) 243:800-817; Rethinasamy, et al., Circ. Res. (1998) 82:116-123).

Here, cultured iPSCs were used to study the role of TPM1 in a well-validated primitive megakaryopoiesis model (Paluru, et al., Stem Cell Res. (2013) 12:441-451; Sim, et al., Blood (2017) 130:192-204). Primitive hematopoiesis occurs in the yolk sac early in development, yielding megakaryocytes that are hyperproliferative and less polyploid than 'definitive' megakaryocytes that develop later in the yolk sac, fetal liver, and bone marrow (McGrath, et al., Curr. Top. Dev. Biol. (2008) 82:1-22). Using this iPSC model, loss of TPM1 is show to hasten and augment hemogenic endothelia and/or hematopoietic progenitor cell (HPC) development, increasing megakaryocyte yield. Thus, a LASSO-based approach has been applied to fine map platelet trait GWAS loci and relevant functional activity of a specified gene has been validated. TPM1 manipulation represents a novel strategy to enhance megakaryocyte production, particularly in vitro. Additionally, a similar LASSO-based approach can elucidate causal variants, genes, and mechanisms for other complex diseases and traits.

Materials and Methods

SNP Selection

GWAS SNPs were identified from Gieger, et al., Nature (2011) 480:201-208 (see Table 1). When two SNPs had been identified in a given region, the SNP with the greater effect size was chosen, resulting in a list of 73 SNPs comprising the model training set. The remaining 8 SNPs were designated as a holdout set. SNPs linked with platelet traits (PLT, MPV, PDW, PCT) from a more recent GWAS9 comprised the validation set.

Human genome version hg19 was used for all other analyses and the LiftOver feature was utilized when necessary.

Linkage Disequilibrium Structure Assessment

The SNP Annotation and Proxy Search tool (archive.broadinstitute.org/mpg/snap/ldsearch.php), LDlink (analysis-tools.nci.nih.gov/LDlink), and 1000 Genomes Phase III data were used to analyze linkage disequilibrium in this study.

Control SNP Selection

Approximately 10,000 control SNPs were identified for each training set GWAS SNP using the Genomic Regulatory Elements and Gwas Overlap algoRithm (GREGOR) (Schmidt, et al., Bioinformatics (2015) 31:2601-6), which matched SNPs based on Distance to Nearest Gene, "LD buddies" (i.e., number of SNPs within a LD block) and Minor Allele Frequency.

Machine Learning Using LASSO

A total of 780,705 GWAS and control SNPs were analyzed for overlap with 627 different chromatin features compiled from ENCODE cell types (Feingold, et al., Science (2004) 306:636-40) or primary human megakaryocytes (Tijssen, et al., Dev. Cell (2011) 20:597-609). Columns representing the 3 baseline parameters (Distance to Nearest Gene, LD Buddies and Minor Allele Frequency) were also included in this data table for each SNP. These 3 baseline characteristics were based on 1000 Genomes EUR population data.

The chromatin feature overlap data were then analyzed using the least absolute shrinkage and selection operator (LASSO, glmnet version 2.0-2) (Tibshirani, R., J. R. Stat. Soc. B (1996) 58:267-288; Zou, et al., J. R. Stat. Soc. Ser. B Stat. Methodol. (2005) 67:301-320) with 10-fold cross-validation and forced inclusion of the 3 baseline parameters, which were assigned penalty factors of 0. Other chromatin features were assigned penalty factors of 1. Coefficients were taken from the $\lambda$se (Df 12, % Dev 0.062980, $\lambda$ 6.203e-05).

Transcription Factor Binding Site Identification

Transcription factor binding sites were identified using the Find Individual Motif Sequences (FIMO) and Analysis of Motif Enrichment (AME) tools from MemeSuite (meme-suite.org). To identify GATA sites, the genomic sequence contexts for LD blocks containing each GWAS SNP were analyzed for matches (p<0.001) with the canonical GATA binding motif in all orientations (AGATAA, TTATCA, AATAGA, TTATCT) or near-canonical motifs (e.g. GATAA) by manual curation.

Score Validation, Including Regulatory Region Analysis, Enhancer Analysis and Molecular Pathway Identification Gene Ontology (GO, www.geneontology.org) pathways were used (Ashburner, et al., Nat. Genet. (2000) 25:25-29). A total of 132 "megakaryocyte genes" were collected from pathways that were returned after a search for the term "megakaryocyte", including "positive regulation of megakaryocyte differentiation", "negative regulation of megakaryocyte differentiation", "regulation of megakaryocyte differentiation", "megakaryocyte differentiation", "megakaryocyte development", "platelet alpha granule", "platelet formation", "platelet morphogenesis" and "platelet maturation". Gene locations were obtained from the UCSC Genome Browser Table Browser feature.

The Genomic Regions Enrichment of Annotation Tool (GREAT; McLean, et al., Nat. Biotechnol. (2010) 28:495-501) was used in combination with the UCSC Genome Browser (Table Browser interface; Kent, et al., Genome Res. (2002) 12:996-1006) to analyze SNP locations and proximity to known genes.

Enhancer regulatory regions were defined according to the FANTOM5 data set (Andersson, et al., Nature (2014) 507:455-61). Presented FANTOM5 data represent the top 1000 highest scoring SNPs that were included as part of the GWAS MPV analysis cohort.

Human iPSC Generation iPSC models were generated as described from peripheral blood mononuclear cells (Maguire, et al., Stem Cell Res. (2016) 16:338-341). The "CHOP10" and "CHOP14" lines were used in this study. Briefly, peripheral blood mononuclear cells (PBMCs) were collected from healthy donors. The PBMCs were expanded for 7 days in media containing erythropoietin (EPO), insulin-like growth factor 1 (IGF-1), SCF, IL-3, dexamethasone, ascorbic acid, glutamine and penicillin/streptomycin. Expanded cells were then reprogrammed via transduction with Sendai virus expressing human Oct3/4, Sox2, Klf4 and c-Myc. These transduced cells were then maintained in culture containing irradiated mouse embryonic fibroblasts (MEFs) until uniform colonies were generated. The iPS colonies were then mechanically isolated, expanded on MEFs, and analyzed to ensure fidelity and pluripotency.

CRISPR/Cas9-mediated genome editing was performed as described (Maguire, et al., Curr. Protoc. Stem Cell Biol. (2019) 48:e64) per protocols from the CHOP Human Pluripotent Stem Cell Core Facility (ccmt.research.chop.edu/cores_hpsc.php) with the following guide sequences:

```
                                        (SEQ ID NO: 4)
5' (1) ATGACGAAAGGTACCACGTCAGG (chr15:63,059,283-63,059,305);

(SEQ ID NO: 5)
5' (2) TGAGTACTGATGAAACTATCAGG (chr15:63,059,321-63,059,343);

(SEQ ID NO: 6)
3' (1) CCCTTTTCTTGCTGCTGTGTTGG (chr15:63,063,953-63,063,975);

(SEQ ID NO: 7)
3' (2) GGAGAGTGATCAAGAAATGGAGG (chr15:63064003-63064025),
``` wherein chromosome locations are in build Human GRCh38/hg38.

Karyotyping (Cell Line Genetics, Madison, WI) and copy number variation (CHOP Center for Applied Genomics, Philadelphia, PA) analyses were performed per institutional protocols.

iPSC Hematopoietic Differentiation and Analysis iPS cells were differentiated in HPCs and megakaryocytes per published protocols (Paluru, et al., Stem Cell Res. (2013) 12:441-451; Sim, et al., Blood (2017) 130:192-204). Briefly, iPS cells were initially maintained on MEFs, as described above, and then transitioned to feeder-free Matrigel® prior to differentiation. When iPS cells were ~70% confluent, they were sequentially cultured in media containing bone morphogenetic protein 4 (BMP4), vascular endothelial growth factor (VEGF) and Wnt3a (Wnt Family Member 3A) in RPMI medium (Days 0-1); BMP4, VEGF and basic fibroblast growth factor (bFGF) in RPMI medium (Day 2); BMP4, VEGF and bFGF in SP34 medium (Day 3); VEGF and bFGF in SP34 medium (Days 4-5); VEGF, bFGF, stem cell factor (SCF) and FMS-like tyrosine kinase 3 ligand (Flt3L) in SFD medium (Day 6); and VEGF, bFGF, SCF, Flt3L, thrombopoietin (TPO) and IL-6 in SFD medium (Days 7-10). To generate megakaryocytes, HPCs in suspension were treated with CSF, TPO and interleukin-3 (IL-3) in SCF medium for up to 5 days.

Flow Cytometry

Flow cytometry analyses and FACS-sorting was performed on a FACS Aria II (BD Biosciences). Flow cytometry data were analyzed using FlowJo 10 (Tree Star, Inc.). The following antibodies from BD Biosciences or BioLegend were used for flow cytometry: FITC-conjugated anti-CD41a, PE-conjugated anti-CD42b, PerCP-Cy7-conjugated anti-CD34, APC-conjugated anti-CD235, and PB450-conjugated anti-CD45.

Microarray Analysis

For microarray analysis, 50,000 cells were FACS-sorted directly into Trizol. RNA was extracted from using a miRNeasy™ Mini Protocol (Qiagen). Samples passing quality control were analyzed using the human Clariom D Assay (ThermoFisher Scientific) and analyzed using Transcriptome Analysis Console (ThermoFisher Scientific) Software or by user-generated scripts.

Cell Imaging and Analysis

For cytospins, FACS-sorted megakaryocytes were spun onto a glass slide and stained with May-Grünwald and Giemsa. Images were obtained on an Olympus BX60 microscope with a 40× objective. An Invitrogen EVOS microscope with a 10× objective was used to image cells in culture. Colony assays and lineage expansions were performed as described (Paluru, et al., Stem Cell Res. (2013) 12:441-451; Mills, et al., Blood (2013) 122:2047-51).

Western Blots

Cell pellets were resuspended in Laemmli buffer, sonicated for 5 minutes, and boiled for 5 minutes at 95° C. Lysates were centrifuged at 10,000 rpm for 5 minutes at room temperature, and supernatants were used for analysis. Lysate volumes were normalized to cell counts. Samples were run on 4-12% NuPAGE® Bis-Tris gels (Invitrogen) and transferred onto nitrocellulose membranes (0.45 um pore size, Invitrogen) at 350 mA for 90 minutes. Following blocking in 5% milk for 1 hour, membranes were incubated with primary antibodies overnight at 4° C. After washing thrice in tris-buffered saline (TBS) and Tween® 20 (TBST), membranes were incubated with secondary horseradish peroxidase-conjugate antibodies for 1 hour at room temperature, washed in TBST thrice, and developed using ECL western blotting substrate (Pierce) and HyBlot CL autoradiography film (Denville Scientific). The following antibodies were used for western blotting: rabbit anti-TPM1 (D12H4, #3910, Cell Signaling Technologies), rabbit anti-TPM4 (AB5449, Millipore Sigma), and mouse anti-beta Actin (A1978, Sigma). Western blot band quantitation was performed using FIJI.

Data Presentation

Genome-wide SNP Scores were loaded as custom tracks into the UCSC Genome Browser (Kent, et al., Genome Res. (2002) 12:996-1006). Images depicting genomic loci were generated using this tool, as well as Gviz (Hahne, et al., Visualizing Genomic Data Using Gviz and Bioconductor in Statistical Genomics: Methods and Protocols (eds. Mathe & Davis) 335-351 (Springer, 2016)). Other data were created and presented using R, Adobe Illustrator CS6 or GraphPad Prism 6.

Statistics

Statistical analyses were conducted using R or GraphPad Prism 6.

Results

Machine Learning Identifies Key Chromatin Features that Impact Platelet Trait Variation Penalized logistic regression (LASSO) was used to identify which of 627 different chromatin features best distinguished 73 platelet trait GWAS SNPs (Gieger, et al., Nature (2011) 480:201-208) from controls (FIG. 1B). The predictive model incorporated 9 epigenetic features with an AUC of 0.793 (FIG. 1C and Table 1). Each of these features had a positive coefficient, meaning that each positively impacted the likelihood that an overlapping SNP was a GWAS SNP.

TABLE 1

Nine chromatin features discriminate platelet trait GWAS SNPs from controls. In addition to background characteristics, 9 chromatin features were identified after LASSO analysis at the λse. The cell type for each feature data set and function for each feature are displayed in the table. The coefficient for each feature, related to its relative importance, is shown at right.

| Cell type | Mark | Function | Coefficient |
|---|---|---|---|
| 1° MK | GATA1 | Ery/MK TF | 5.08e−01 |
| 1° MK | FLI1 | Ery/MK TF | 6.17e−02 |
| K562 | H3K36me2 | Active gene bodies | 4.11e−01 |
| K562 | H3K79me2 | Enhancers | 1.15e−01 |
| K562 | RbBP5 | SET1 methylation complex | 4.45e−01 |
| Gm12878 | H3K4me1 | Enhancers, 5' active genes | 3.08e−01 |
| Gm12878 | H3K4me2 | Enhancers, promoters, TF binding sites | 5.36e−01 |
| Gm12878 | H3K27ac | Active genes, enhancers, TF binding sites | 1.14e−01 |
| HUVEC | H3K4me2 | Enhancers and promoters | 8.59e−02 |

Ery: erythroid.

This LASSO-based model was biologically plausible. GATA1 and FLI1 are critical megakaryocyte transcription factors (Tijssen, et al., Dev. Cell (2011) 20:597-609; Pimkin, et al., Genome Res. (2014) 24:1932-1944), and most of the features came from hematopoietic cells (primary megakaryocyte, K562, GM12878; Table 1). Furthermore, the set of 9 chromatin features would be functionally predicted to identify regulatory elements near and within gene bodies (Table 1).

To quantitatively stratify loci genome-wide, SNP scores were assigned based on overlap with these 9 features, using coefficients as multipliers (e.g., if a SNP 'perfectly' overlapped all features, its score would be 2.58403122).

LASSO Identifies Relevant Platelet Trait-Specific Loci and Genes

It was then determined which predictive model best discriminated known platelet trait GWAS loci and which model most specifically identified relevant loci. The LASSO model scored platelet trait GWAS SNPs from the training set, or a holdout set, significantly higher than SNPs genome-wide (FIG. 2A). More importantly, the LASSO model outperformed other predictive models (Kircher, et al., Nat. Genet. (2014) 46:310-315; Ritchie, et al., Nat. Methods (2014) 11:294-296; Zhou, et al., Nat. Methods (2015) 12:931-934) in identifying these SNPs in training and holdout sets. GWAVA also performed well in these analyses, as well as in a validation GWAS SNP cohort.

Next, it was determined which model(s) best identified megakaryocyte- and platelet-related loci. To do this, all SNPs among the top 10% of scores were identified (e.g., for GWAVA, any SNP assigned a score 0.90-1.00). LASSO (11168 SNPs, 0.08% of SNPs analyzed) and CADD (39563 SNPs, 0.05%) were much more specific at this scoring level than GWAVA (230507 SNPs, 0.46%) (FIG. 2B). These results indicated that LASSO and CADD are more specific in locus identification than GWAVA.

The top-scoring 4000 SNPs from each of these 3 models were then used to identify related Gene Ontology biological pathways. LASSO and GWAVA each identified several hematopoietic pathways, although high-scoring SNPs from the LASSO model were much more targeted to megakaryocytic biology (FIG. 2C). Genes related to high-scoring SNPs from the GWAVA model were more related to lymphoid biology (e.g., for "HPC differentiation", "hemopoiesis", and "hematopoietic or lymphoid organ development"). In contrast, high-scoring SNPs from the CADD model did not identify any enriched hematopoietic pathways.

In sum, published models identified regulatory elements in a non-cell-specific manner. These findings also indicated that SNPs that scored highly in the LASSO model specify functional loci that impact megakaryocyte and/or platelet biology.

A LASSO-Based Predictive Model Correlates with GWAS Findings and Identifies Loci Related to Megakaryocyte and Platelet Biology The LASSO-based SNP scores correlated with summary level platelet trait GWAS data. This supported the position that the scoring algorithm was valid genome-wide and could reveal true biological associations, as had the GWAS itself (Gieger, et al., Nature (2011) 480:201-208; Simon, et al., Am. J. Hum. Genet. (2016) 98:883-897; Soranzo, et al., Blood (2009) 113:3831-3837; Nurnberg, et al., Blood (2012) 120:4859-4868).

Although SNPs with genome-wide significant p-values 5e-8) had higher scores on average than any others, SNPs with marginal p-values (5e-8-0.05) also scored significantly higher on average than SNPs with non-significant p-values greater than 0.05. This indicated that these 'near miss' SNPs may include some biochemically active loci.

It is generally thought that non-coding functional SNPs associate with enhancer or other regulatory regions (Tak, et al., Epigenetics Chromatin (2015) 8:57; Farh, et al., Nature (2014) 518:337-343). Indeed, FANTOMS enhancer regions were enriched for high scoring SNPs, with an average score>0.9 compared with an average score 0.21 genome-wide (Andersson, et al., Nature (2014) 507:455-61). However, enhancer regions from a human megakaryoblastic leukemia cell line (CMK, the closest FANTOM5 cell type to primary megakaryocytes) did not score significantly higher than enhancer regions from other cell types. This argues against high trait specificity in these regions.

Most high-scoring SNPs from the LASSO model were in gene bodies or near transcriptional start sites (TSSs) (McLean, et al., Nat. Biotechnol. (2010) 28:495-501). SNPs near TSSs or within the coding sequence (CDS) for key megakaryocyte genes were determined to score significantly higher than SNPs in matched regions for random genes. Thus, the LASSO model successfully relevant loci, particularly those near and within gene bodies.

Fine Mapping Using LASSO-Based SNP Scores, GATA Binding Sites and eQTL Data Identifies Causal Platelet Trait Variation Loci It was reasoned that active variants would i) be in high linkage disequilibrium (LD) with established platelet trait GWAS loci, ii) score highly relative to other SNPs in a given LD block, iii) regulate target gene(s) as quantitative trait loci, and (iv) overlap GATA binding sites (Mathelier, et al., Nucleic Acids Res. (2016) 44:D110-D115; Grant, et al., Bioinformatics (2011) 27:1017-8). GATA binding sites were prioritized based the importance of GATA factors in megakaryopoiesis (Tijssen, et al., Dev. Cell (2011) 20:597-609; Freson, et al., Blood (2001) 98:85-92) and in the scoring algorithm (FIG. 1C).

Figures 3D, 3E, 3F:
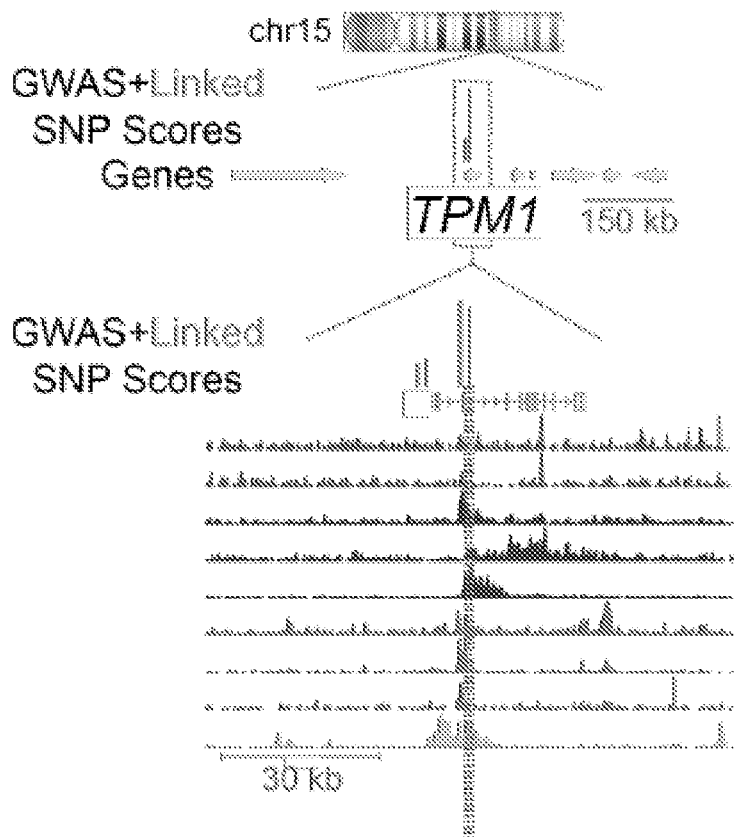
FIG. 3D shows a chromosome 15 ideogram, SNP scores and genes near platelet trait GWAS SNP rs3809566. The GWAS SNP is shown in black, linked SNPs ($r^2>0.8$) are shown, and two high-scoring SNPs with weaker linkage ($r^2<0.8$) are shown. Gene CDSs are also shown. The boxed region containing the TPM1 gene locus is expanded to show local genomic context, including relevant SNPs and TPM1 exons along with chromatin feature tracks that contributed to SNP scores.
FIG. 3E shows the local DNA sequence, including the rs11071720 SNP site (underlined) and a putative GATA binding site. Provided sequence is SEQ ID NO: 9.
FIG. 3F provides the major and minor rs11071720 alleles, with consequences on TPM1 expression and associated platelet phenotypes. Allele percentages based on UCSC genome browser and dbSNP.

This approach led to SNPs known to impact megakaryocyte development and/or platelet function (Table 2). For example, rs342293 is a GWAS SNP7 that regulates PIK3CG gene expression (FIGS. 3A-3C) (Soranzo, et al., Blood (2009) 113:3831-3837). In platelets, PIK3CG activity regulates PIK3 signaling and directs cellular movement, adhesion, and contraction, including platelet-induced aggregation and secretion in response to collagen (Hawkins, et al. (2014) Science 318:324-328; Pasquet, et al., Blood (2000) 95:3429-34). The GATA site is disrupted in the presence of the SNP minor allele (FIG. 3D). Platelets from individuals harboring the minor G allele had increased mean platelet volume (MPV) and decreased Annexin V reactivity (Soranzo, et al., Blood (2009) 113:3831-3837).

TABLE 2

(Top) LASSO-based fine-mapping identifies eQTLs in established platelet trait GWAS loci that overlie GATA binding sites.

| rsID# | Chr | BP | LASSO | GWAVA | eQTL Gene Symbol(s) | Evidence (PMID) |
|---|---|---|---|---|---|---|
| rs625132 | 2 | 31482300 | 1.29 | 0.19 | EHD3 | |
| rs72879290 | 2 | 43633268 | 1.37 | 0.27 | PLEKHH2, (RN7SL531P) | 29117201 |
| rs342293 | 7 | 106372219 | 2.00 | 0.94 | PIK3CG* | 19221038 |
| rs7088799 | 10 | 65016174 | 2.01 | 0.27 | NRBF2, (MRPL35P2) | 26209658 |
| rs7899657 | 10 | 65323265 | 1.03 | 0.17 | REEP3 | |
| rs17655663 | 11 | 268940 | 1.58 | 0.72 | SIRT3, NLRP6, BET1L, RIC8A, PSMD13, SCGB1C1, AC136475.3 | 25829495 |
| rs72882962 | 11 | 269129 | 1.68 | 0.48 | SIRT3, NLRP6, BET1L, RIC8A, PSMD13, SCGB1C1 | 25829495 |
| rs6589734 | 11 | 119186403 | 1.90 | 0.95 | CBL, (NLRX1, HINFP, HMBS) | 22931288 |
| rs941207 | 12 | 57023284 | 2.08 | 0.68 | RBMS2, BAZ2A | |
| rs11071720 | 15 | 63341996 | 1.59 | 0.58 | TPM1, LACTB, RAB8B, (APH1B) | 22139419**, 19858488, 8356066 |
| rs4819526 | 22 | 19974032 | 1.90 | 0.89 | COMT, (ARVCF, TANGO2) | 955854 |

TABLE 2-continued (Top) LASSO-based fine-mapping identifies eQTLs in established platelet trait GWAS loci that overlie GATA binding sites.

| rsID# | Chr | BP | eQTL Gene Symbol(s) | pval <0.05* | Evidence |
|---|---|---|---|---|---|
| rs13306560 | 1 | 11866183 | CLCN6, NPPA-AS1, MIIP | MPV, PCT | |
| rs518686 | 1 | 231377081 | GNPAT | | |
| rs59993156 | 3 | 43732924 | ABHD5 | | |
| rs199617773 | 3 | 47018202 | | | |
| rs114336481 | 3 | 127309439 | | | |
| rs79533891 | 4 | 153701259 | | | |
| rs33556 | 5 | 112312528 | MCC | | |
| rs112997548 | 8 | 27168807 | CLU | | |
| rs77774580 | 8 | 101964635 | | | |
| rs28999669 | 8 | 103250991 | RRM2B | MPV, PCT, PLT# | |
| rs4253005 | 10 | 50747071 | | | |
| rs4253004 | 10 | 50747080 | | | |
| rs183383535 | 13 | 20437552 | | | |
| rs191207454 | 13 | 52158712 | LACC1 | | |
| rs11855135 | 15 | 81282256 | MESDC1, MESDC2 | | |
| rs115188539 | 17 | 34890751 | RAB32, TAF15, CCL4L1 | | 11784320 |
| rs11553244 | 19 | 49468642 | | | |
| rs59819533 | X | 78622841 | | | |

Listed are SNPs within GWAS LD blocks ($r^2 > 0.7$) scoring in the top 5% (LASSO) that overlap canonical or near-canonical GATA binding sites and are eQTLs for at least 1 gene. Associated GWAVA scores are also presented. Evidence relates to human cell validation, except where indicated. Genes in bold were affected in whole blood. # SNP names and locations refer to hg19 genome.
*eQTL in human platelets, 16 though not in GTEx tissues.
**Function suggested by D. rerio morpholino experiments. (Bottom) SNPs that scored in the Top 1% for LASSO and GWAVA that did not meet genome-wide significance for platelet trait variation. These SNPs all had 'perfect' LASSO (2.58401322) and GWAVA (1.0) scores. Traits with subgenome-wide significant p-values that were <0.05 are indicated. Evidence refers to functional validation related to MKs or platelets in human cells (PMIDs). None of these sites overlaps a canonical GATA binding site.
MESDC1: mesoderm developmental candidate gene 1.
MESDC2: mesoderm developmental candidate gene 2.
CLCN6: chloride voltage-gated channel 6.
NPPA-AS1: natriuretic peptide A antisense 1 (long noncoding RNA).
RRM2B: ribonucleotide reductase M2 B.
MCC: mutated in colorectal cancer.
GNPAT: glyceronephosphate O-acyltransferse.
ABHD5: abhydrolase domain containing 5. # hg19.
*p-value <0.05 for MPV, PCT, PDW or PLT# traits.

Fine Mapping Identifies Putatively Causal Variants at the TPM1 Gene Locus

Figure 3G:
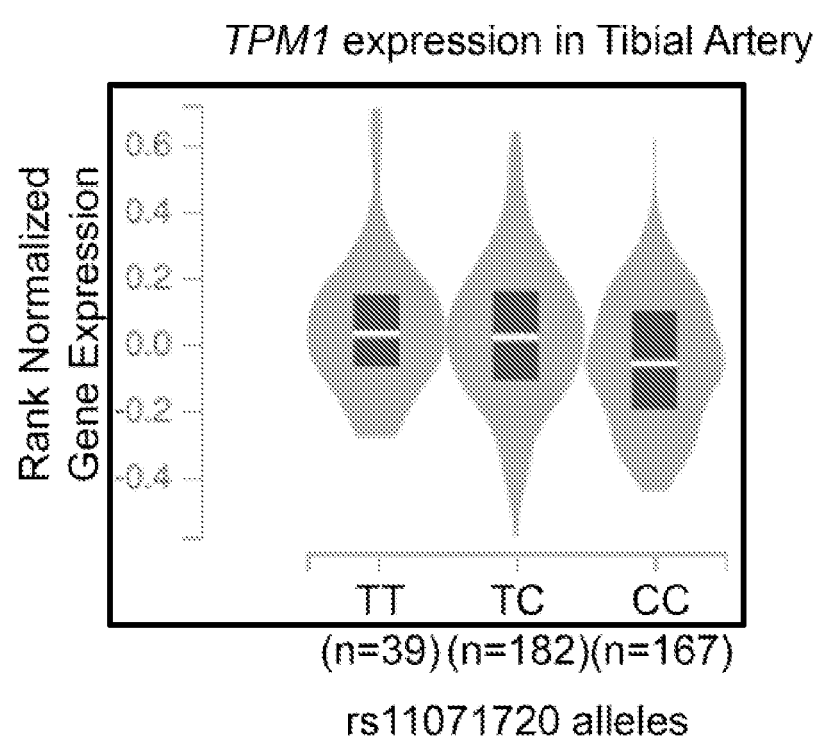
FIG. 3G shows that SNP rs11071720 is an expression quantitative trait locus (eQTL) for TPM1. Individuals with the rs11071720 minor 'C' allele have decreased Tropomyosin 1 expression in tibial artery tissue ($p=0.000056$, Normalized Enrichment Score=−0.082).

This approach also highlighted rs11071720, an intronic SNP within the Tropomyosin 1 (TPM1) gene locus in LD with GWAS SNP7 rs3809566 ($r^2=0.84$; FIGS. 3D-3F). The minor allele, which disrupts a near-canonical GATA binding site, is an expression quantitative trait locus (eQTL) associated with decreased TPM1 expression (Fehrmann et al., PLoS Genet. (2011) 7(8):e1002197; Ardlie, et al., Science (2015) 348:648-660) (FIG. 3G). The minor allele is also linked with higher platelet count and decreased platelet size (mean platelet volume, MPV) (Astle, et al., Cell (2016) 167:1415-1429).

Two other high-scoring SNPs within the TPM1 gene locus warrant mention, despite missing the initial LD threshold of $r^2>0.8$ with GWAS SNP rs3809566 (FIG. 3D, gray bars). The minor allele for rs4075583 (score 1.71, $r^2=0.74$ with rs3809566) was associated with decreased TPM1 expression in heterologous cells, but not in GTEx tissues (Ardlie, et al., Science (2015) 348:648-660; Savill, et al., Am. J. Hypertens. (2010) 23:399-404). High scoring rs4075047 has weaker linkage (score 1.71, $r^2=0.25$ with rs3809566) and made no impact on TPM1 expression (Savill, et al., Am. J. Hypertens. (2010) 23:399-404). None of these SNPs, nor TPM1, had been functionally evaluated in the context of hematopoiesis.

TPM1 is Normally Downregulated During Hematopoiesis

Figure 4A:
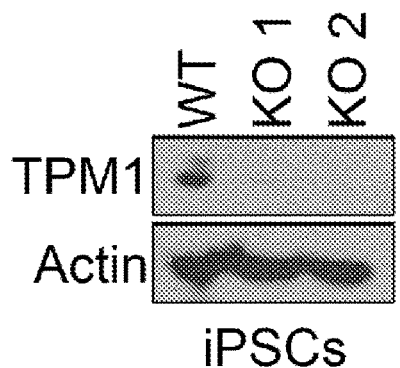
FIG. 4A provides a Western blot of wild type (WT) and knockout (KO) induced pluripotent stem cells (iPSCs)
Figure 4B:
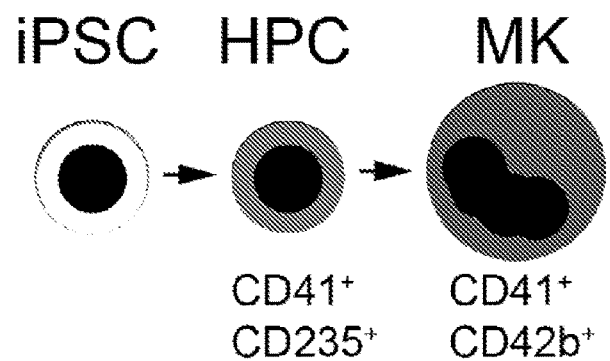
FIG. 4B provides a schematic of iPSC differentiation and MK expansion. HPC: hematopoietic progenitor cell.
Figure 4C:
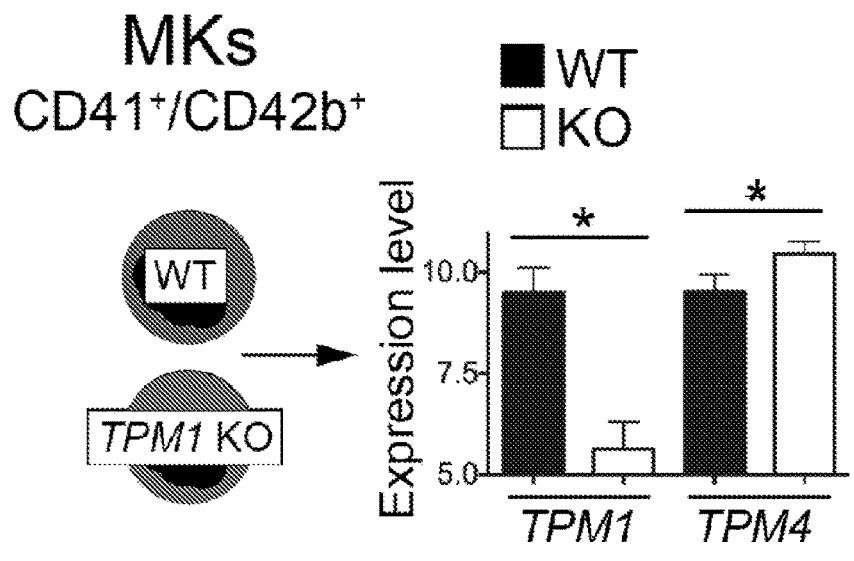
FIG. 4C shows expression levels of TPM1 and TPM4 in mature CD41$^+$/CD42b$^+$ WT and KO MKs collected by FACS-sorting on day 5 of expansion culture and analyzed by microarray. *p<0.05.
Figure 4D:
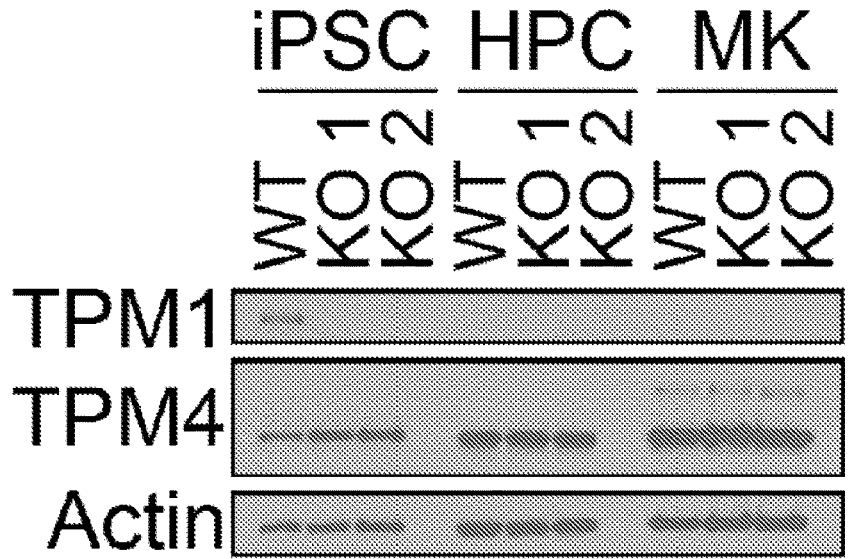
FIG. 4D provides a Western blot of lysates from iPSC, HPCs (differentiation d8), and FACS-sorted MKs (expansion d3).
Figure 4E:
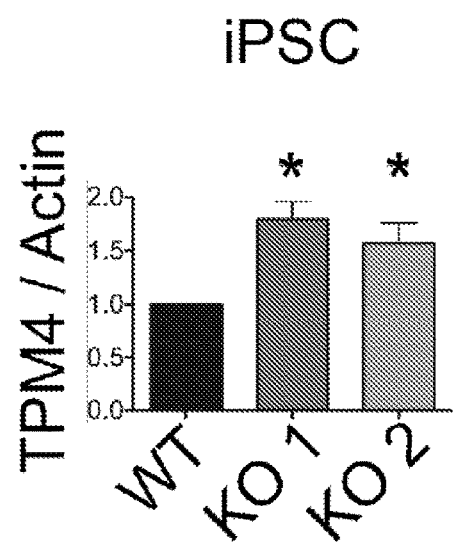
FIG. 4E provides a quantitative analysis of TPM4 band intensities, normalized to actin band intensity. Results are from 3 replicates. *p<0.05 by 1-way ANOVA.
Figure 4F:
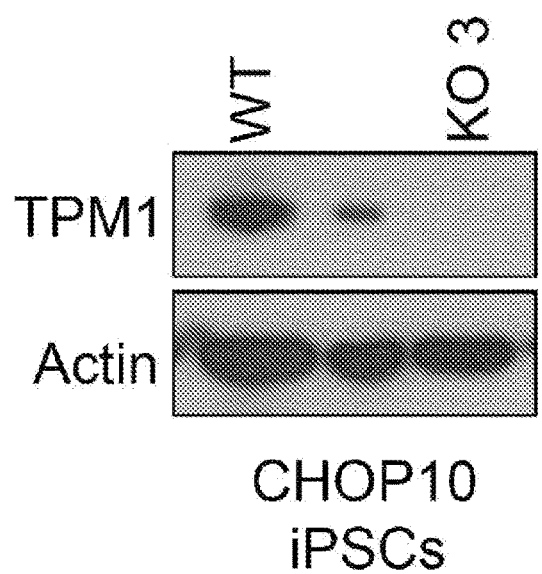
FIG. 4F provides a Western blot of CHOP10 iPSC lysates showing no TPM1 protein in KO clone.

Given that high-scoring putatively causal SNPs (rs11071720 and rs4075583) impacted TPM1 expression, it was investigated whether TPM1 regulated human megakaryopoiesis in an in vitro human model of primitive megakaryopoiesis (Sim, et al., Blood 130:192-204). Using CRISPR/Cas9, a ~5 kb region within TPM1 in iPSCs was targeted and deletion was confirmed by sequencing and western blot (FIGS. 4A and 4F). In total, 3 clones from 2 separate genetic backgrounds were obtained. It was confirmed that these clones had no off-target genomic aberrancies by karyotype and copy number variation analyses.

Figure 4G:
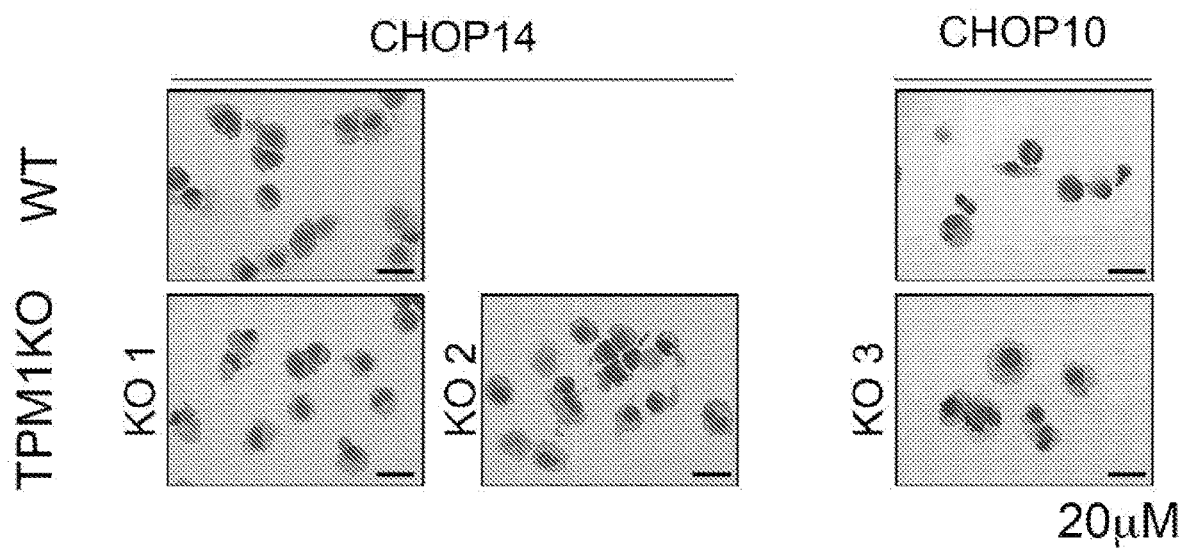
FIG. 4G provides images of wild type (WT) and TPM1 KO CD41$^+$/CD42b$^+$ primitive megakaryocytes, following 8 days differentiation and 5 days megakaryocyte expansion culture, which were FACS-sorted and analyzed by cytospin. Bar represents 20 µm.

Wild type (WT) and KO iPSCs were then differentiated into HPCs and megakaryocytes (FIG. 4B) (Sim, et al., Blood 130:192-204). KO megakaryocytes had grossly normal cell surface marker expression and cellular morphology upon differentiation and expansion (FIG. 4G). Microarray gene expression analysis on FACS-sorted WT and KO megakaryocytes revealed no statistically significant changes in megakaryocyte genes, though Gene Set Enrichment Analysis (GSEA) plots showed a trend toward higher megakaryocyte-related pathway expression in KO megakaryocytes. Indeed, microarray analysis shows no significant differences in megakaryocyte genes and upregulation of Wnt signaling and cardiac conduction pathways. More specifically, the expression of representative megakaryocyte genes platelet factor 4, pro-platelet basic protein, P-selectin, and nuclear factor erythroid 2 are not significantly (ns) changed in WT vs KO megakaryocytes. Overall, 19 molecular pathways were upregulated in KO megakaryocytes (Table 2).

Figure 4H:
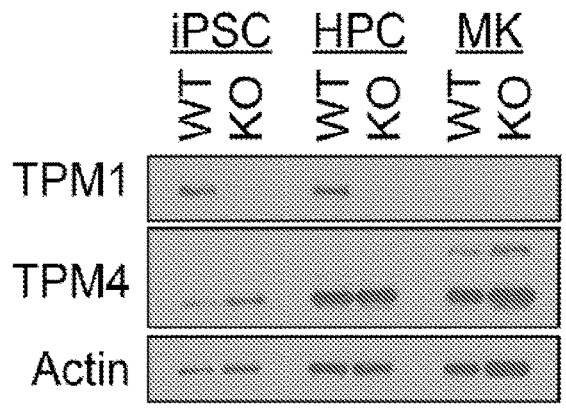
FIG. 4H shows that TPM1 is downregulated during hematopoietic differentiation and TPM4 is upregulated in KO iPSCs. Western blot (left) of lysates from CHOP10 clones show indicated protein expression. 10-fold fewer iPSCs were loaded compared to HPC or megakaryocytes. Quantification of TPM4 level (right) in WT and KO iPSCs, normalized to actin, is also provided.
Figure 4H:
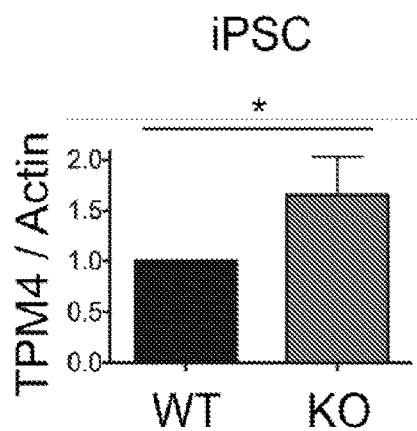

Since Tropomyosin 4 (TPM4) promotes megakaryocyte development and likely also modulates actin dynamics similar to TPM1 (Pleines, et al., J. Clin. Invest. (2017) 127:814-829; Gunning, et al., Curr. Biol. (2017) 27:R8-R13), TPM4 may show changes in TPM1 deficient cells. Indeed, TPM4 expression was significantly upregulated in the microarray analysis (FIG. 4D). Western blots confirmed that TPM1 was present in iPSCs and downregulated during hematopoietic differentiation (FIGS. 4D and 4H). Low molecular weight (LMW) and HMW TPM4 isoforms are upregulated during megakaryocyte differentiation, and LMW TPM4 was significantly increased in TPM1 KO iPSCs (FIGS. 4D and 4E).

Figure 5A:
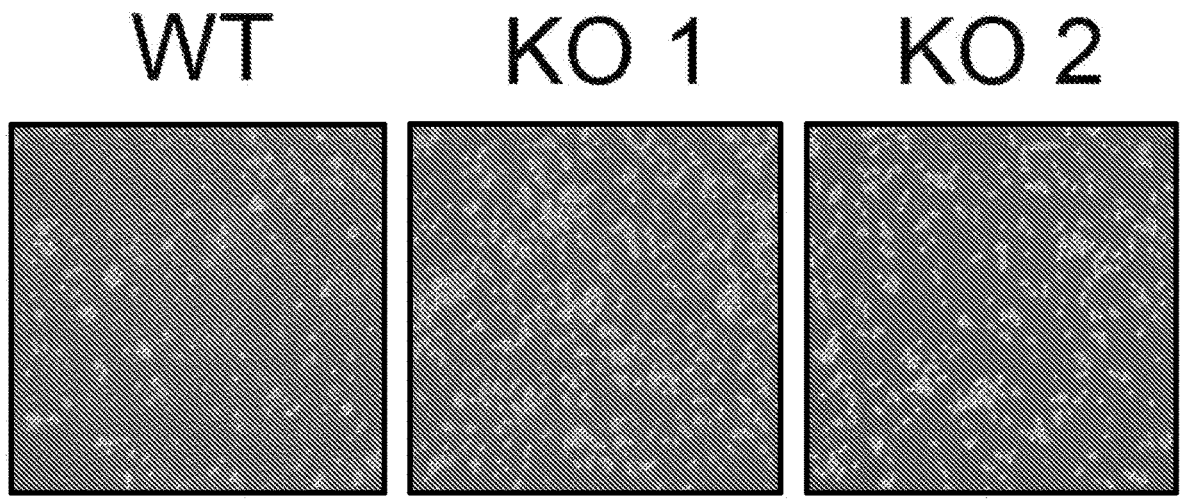
FIG. 5A provides images taken on differentiation day 8, when single cells (typically HPCs, light color) are apparent above the iPSC monolayer.
Figure 5B:
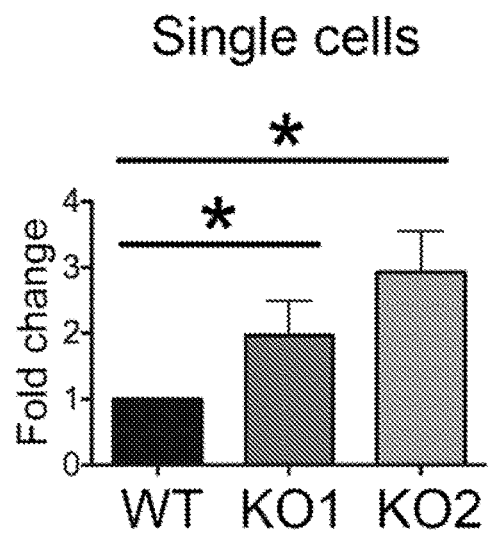
FIG. 5B provides a graph of the quantification of WT and KO single cells on differentiation day 8. Bars represent fold change in single cells (mean±SD) compared to WT. *p<0.05 by ANOVA.

TPM1 loss accelerates megakaryocyte progenitor development Given the predominance of TPM1 protein at the iPSC stage, as well as the compensatory increase in TPM4 at this stage, changes during early hematopoietic differentiation were studied. KO HPC yield roughly doubled that of WT controls by differentiation day 8 (FIGS. 5A, 5B, and 5F). Colony assays revealed fewer colony-generating KO progenitors on day 8, showing that more KO cells had differentiated beyond the true progenitor stage by this time (FIG. 5G). Importantly, mature cell yields from KO cells were not compromised (FIG. 5H).

Figure 5C:
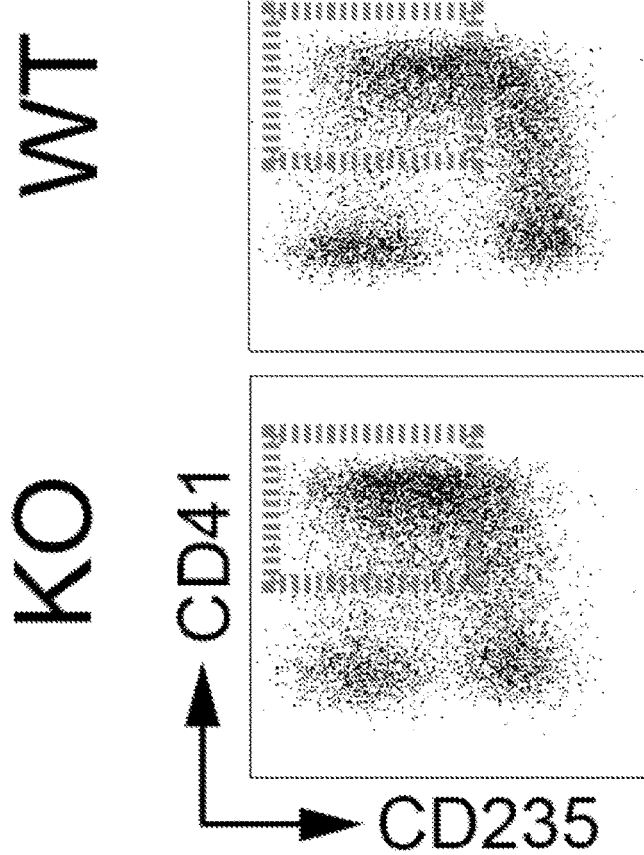
FIG. 5C shows an increased pool of megakaryocyte lineage-directed CD41$^+$/CD235$^-$ cells (boxes) in KO cultures on differentiation day 9.
Figure 5D:
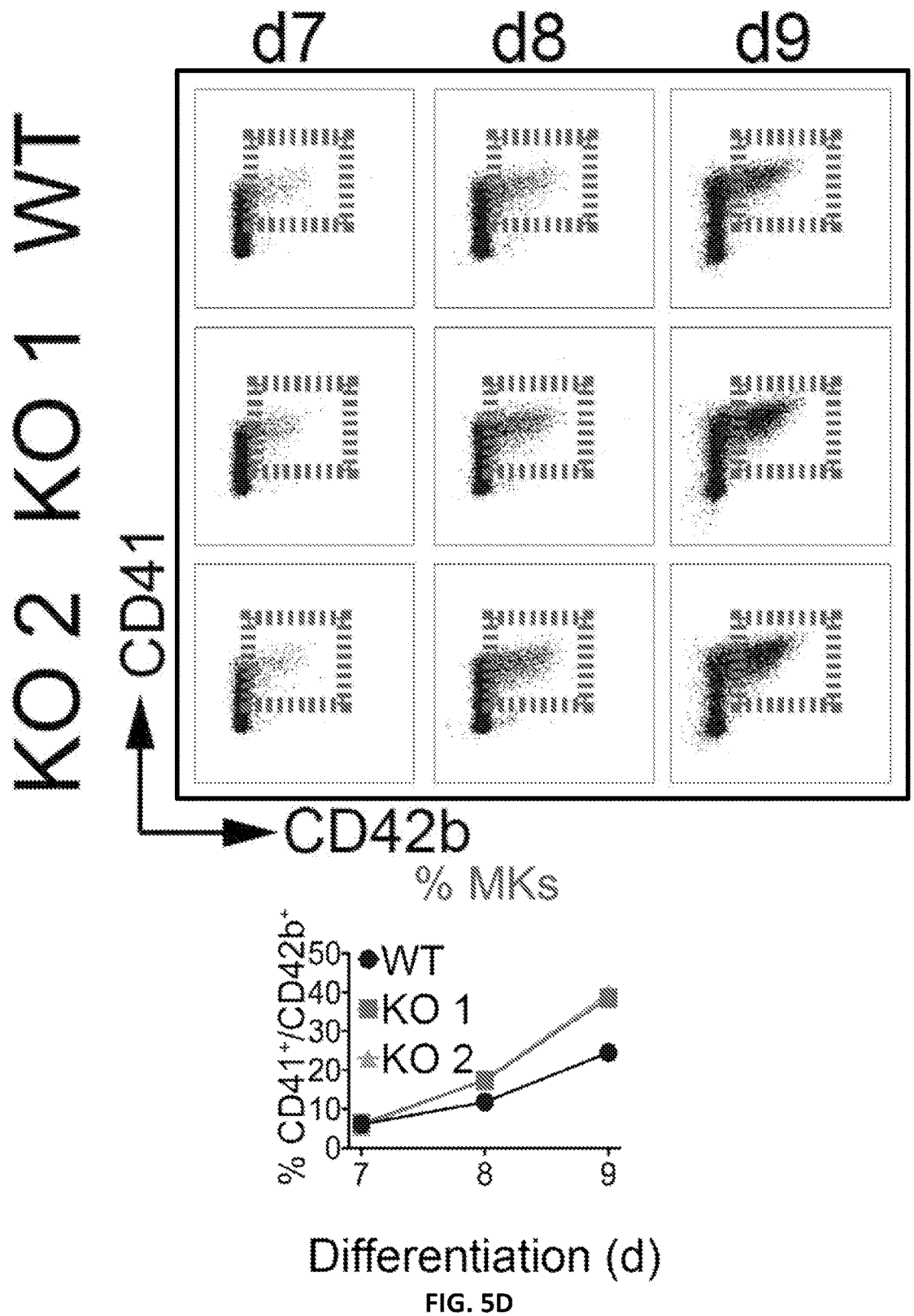
FIG. 5D shows representative flow cytometry plots highlighting mature CD41$^+$/CD42b$^+$ megakaryocytes (boxes) in differentiation cultures from days 7-9. Line plot shows percent (%) CD41$^+$/CD42b$^+$ megakaryocytes for each clone at indicated time points.
Figure 5E:
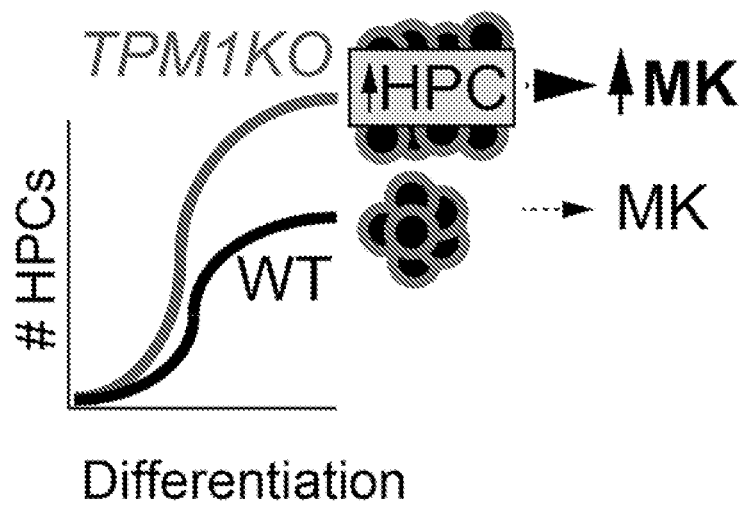
FIG. 5E provides a schematic model in which KO iPSC-derived HPCs emerge earlier and in ultimately greater quantity than WT, generating more total mature megakaryocytes.
Figure 5F:
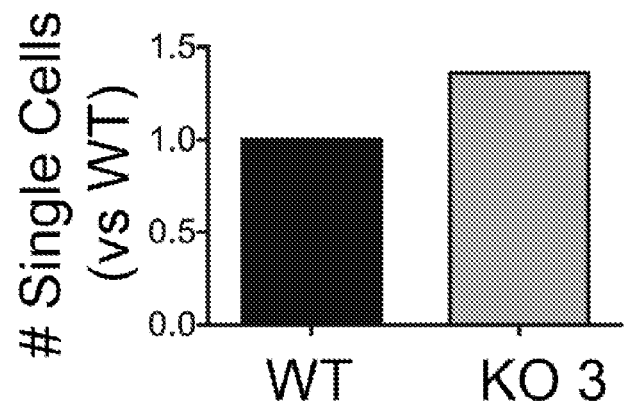
FIG. 5F provides a graph of single cells (typically HPCs) of CHOP10 KO iPSCs on differentiation day 8.

There was a slight predominance of megakaryocyte lineage-directed CD41$^+$/CD235$^-$ cells in KO cultures (FIG. 5C). Indeed, KO HPCs generated mature CD41+/CD42b+ megakaryocytes in thrombopoietin-free media with accelerated kinetics (FIG. 5D). Thus, hematopoietic differentiation occurs faster from KO iPSCs without compromising mature lineage yields (FIG. 5E). Increased megakaryocyte yield would yield more platelets.

Figure 6:
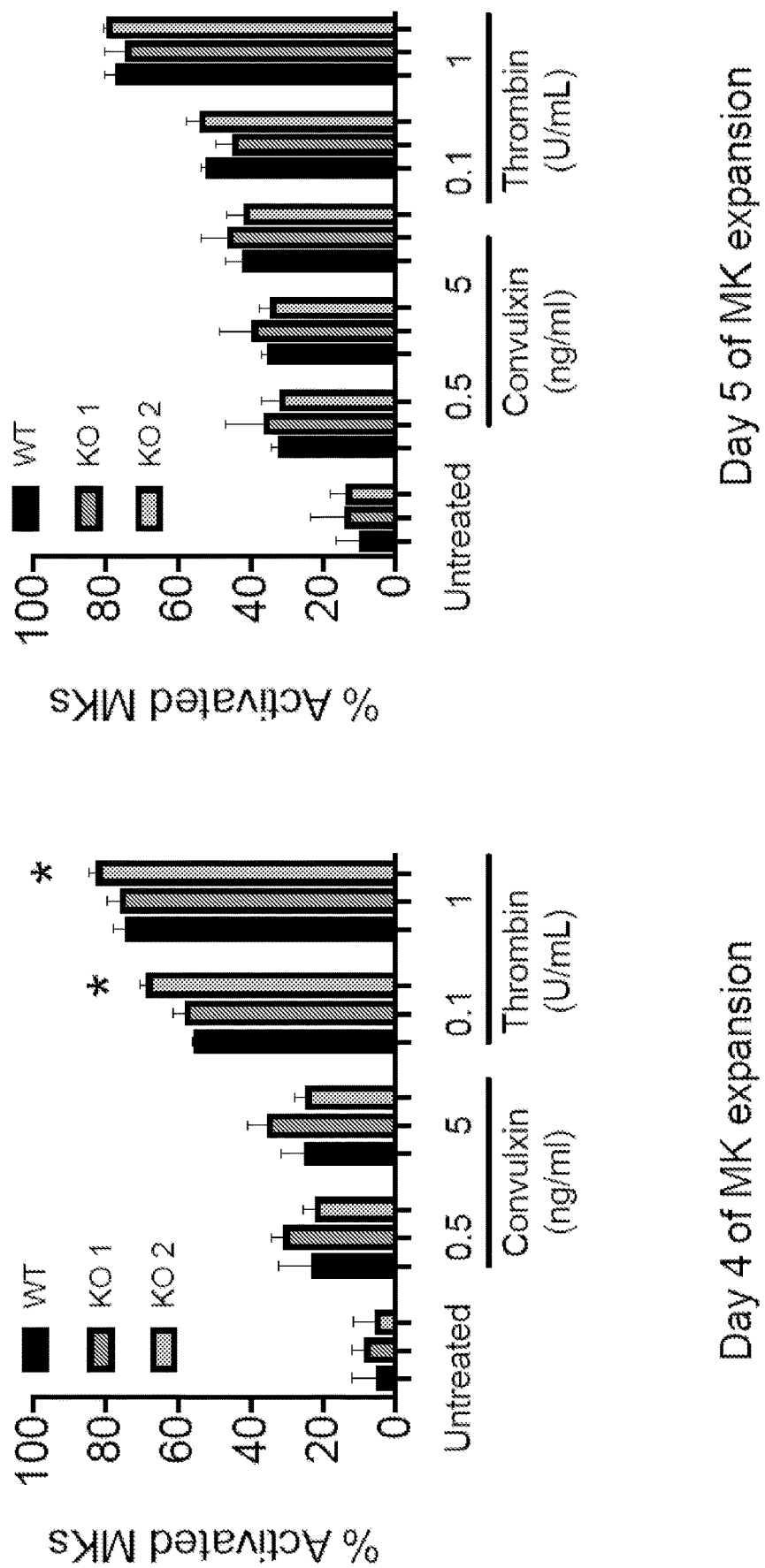
FIG. 6 shows results from experiments where wild type (WT) or knockout (KO) iPSCs were differentiated into hematopoietic progenitors and subsequently expanded into megakaryocytes for 4 to 5 days. At the indicated time points, WT or KO megakaryocytes were activated with convulxin or thrombin at the indicated concentrations for 20 minutes and then analyzed by flow cytometry. Bars show the percent of CD42a$^+$/CD42b$^+$ megakaryocytes with activated integrin aIIbB3 (PAC-1+) for 3 replicates. *p<0.05. Bars are mean±SD.

In further experiments, iPSC were differentiated into hematopoietic progenitors and then expanded into megakaryocytes for 4 or 5 days. The megakaryocytes were then activated by the addition of thrombin or convulxin, and integrin structure was monitored by flow cytometry, which is an indication of platelet activation. As seen in FIG. 6, TPM1 KO megakaryocytes activate normally in response to agonists. Additionally, the longer the megakaryocytes were expanded, the more mature and active the megakaryocytes became.

Figure 7A:
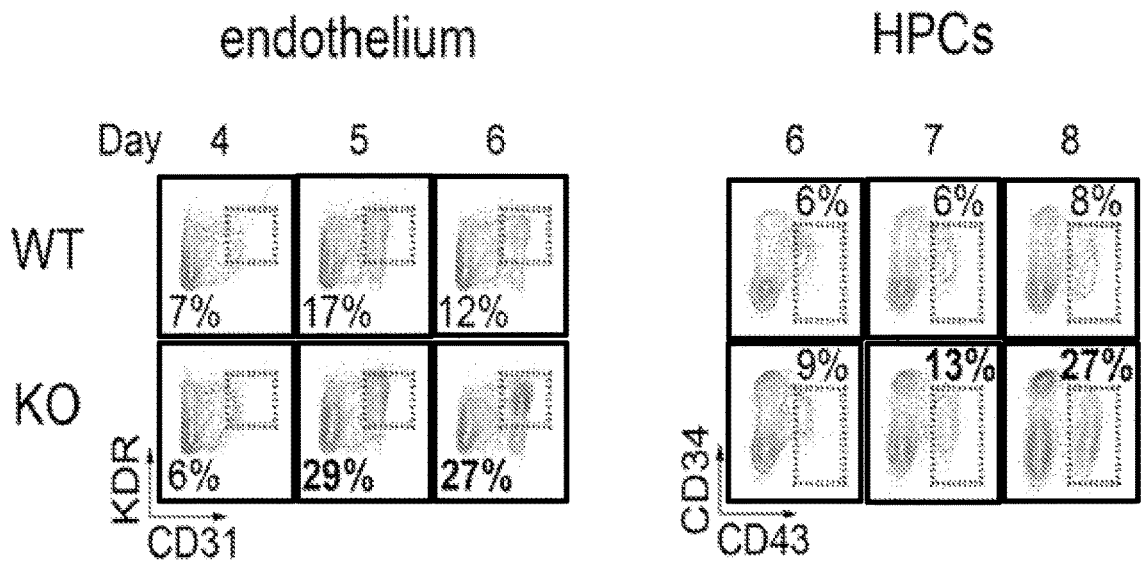
FIG. 7A provides a FACS analysis of KDR, CD31, CD43, and CD34 expression in wild type (WT) and knockout (KO) lines showing an increased percentage of KDR+CD31+ endothelial cells and an increased percentage of CD43+ hematopoietic progenitor cells (HPCs, 27% vs 8%).

In still further experiments, TPM1 knockout (KO) was found to enhance yield of specialized endothelial precursors that form hematopoietic progenitor cells (HPCs). The first noted difference in differentiations of wild type (WT) and KO lines was that KO cells had an increased percentage of KDR (VEGFR2)+CD31+ endothelial cells and an increased percentage of CD43+ hematopoietic progenitor cells (HPCs, 27% vs 8%) (FIG. 7A). The increased endothelial cells at day 5 were consistent in two isogenic KO lines, as well as in WT and KO cells from a genetically distinct iPSC line. These data indicate that TPM1 KO resulted in increased numbers of specialized 'hemogenic endothelial' cells that generate HPCs (Ditadi, et al. (2015) Nat. Cell Biol. 17:580-591).

Figure 7B:
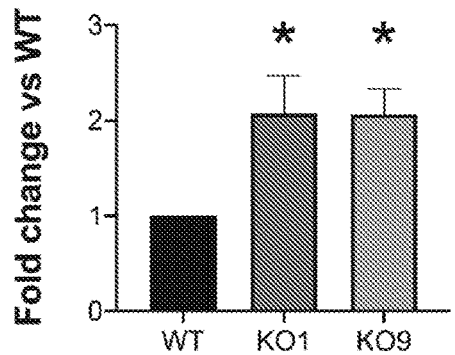
FIG. 7B provides a graph of the HPC precursor cell frequency in KO lines compared to WT. *p<0.05 by ANOVA.
Figure 7C:
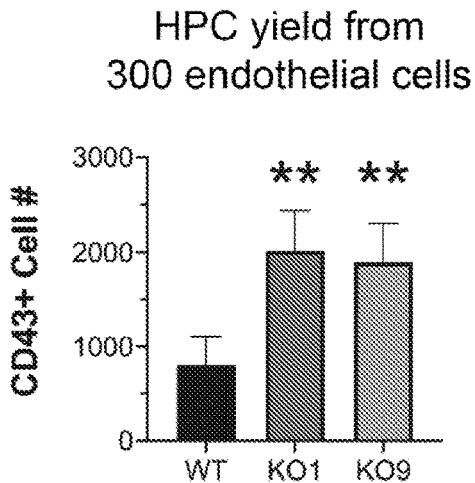
FIG. 7C provides a graph of the yield of CD43+ HPCs derived from 300 FACS-sorted KO endothelial cells vs WT. **p<0.01 by ANOVA.

To quantify endothelial HPC precursors, a limiting dilution analysis was used (Ditadi, et al. (2015) Nat. Cell Biol. 17:580-591; Hu, et al. (2009) J. Immunol. Methods 347:70-78). On differentiation day 4.5, KDR+CD31+CD43− endothelial cells were FACS-sorted into 96-well plates at 3, 10, 30, 100, 300, 1000 cells per well×10 wells each. The sorted cells were cultured in hematopoietic cytokines (SCL/VEGF/Flt3L (Mills, et al., Hematopoietic Differentiation of Pluripotent Stem Cells in Culture. in *Hematopoietic Stem Cell Protocols*, eds. Til, N. P. Van & Wagemaker, G., 1185, 311-319 (Humana Press, 2014)) for 7 days. Each well was then harvested and analyzed for CD43+ expression, a marker of HPCs but not endothelial cells. By limiting dilution analysis there was a ~2-fold enrichment of HPC precursor cell frequency (FIG. 7B). By FACS analysis, ~2-3 times as many CD43+ HPCs were derived from 300 FACS-sorted KO endothelial cells vs WT (FIG. 7C). This relative quantity was consistent with prior analyses of total non-adherent HPC yields in KO vs WT cultures.

Donor-derived platelet supplies are insufficient for clinical demand (Ito, et al., Cell (2018) 174:636-648). Genetic manipulation may increase efficiency of iPSC-derived megakaryocytes and platelets, as has been shown for red blood cells (Giani, et al., Cell Stem Cell (2016) 18:73-78). Many loci are genetically linked with platelet trait variation, but few platelet trait GWAS-identified genes and loci have been biologically validated. Herein, functional genes and loci related to megakaryocyte and platelet biology were identified and validated. Modulation of TPM1 was determined to impact megakaryocyte development. Other candidates are provided in Table 2. Additionally, an analogous approach can investigate functions of high-scoring candidates that overlap binding sites for other key megakaryocyte transcription factors (e.g., ETV6, FLI1 or NFATC2) (Lambert, M. P., Curr. Opin. Hematol., (2015) 22:460-466; Zaslaysky, et al., Blood (2013) 121:3205-3215).

The gene expression analysis identified 19 pathways that were significantly upregulated in TPM1 KO megakaryocytes (Table 2). Of these, non-canonical Wnt signaling is well studied although is typically a potent negative regulator of primitive megakaryocyte development (Table 2). Still, perturbed actin dynamics can promote noncanonical Wnt signaling, which may in turn impact megakaryocyte growth (Paluru, et al., Stem Cell Res. (2013) 12:441-451; Galli, et al., Acta Biomater. (2012) 8:2963-2968; Seo, et al., Blood Adv. (2018) 2:2262-2272).

TPM1 deficiency can leave filamentous actin more accessible to the effects of modulators (England, et al., J. Mol. Cell. Cardiol. (2017) 106:1-13; Gateva, et al., Curr. Biol. (2017) 27:705-713), such as other TPMs. Of these, TPM4 promotes megakaryocyte development and was significantly upregulated in KO iPSCs and megakaryocytes (FIGS. 4C-4E). An expanded pool of TPM4 may also have enhanced influence on actin dynamics such that it may account for enhanced HPC and megakaryocyte yield (FIG. 5G).

TPM1 expression is regulated by rs11071720 in some tissues (Ardlie, et al., Science (2015) 348:648-660). Notably, TPM1 has not been linked with human blood cancers although it does function as a tumor suppressor in other contexts (Du, et al., Oncol. Rep. (2015) 33:2807-2814; Chen, et al., Med. Sci. Monit. (2018) 24:7875-7882). This would be consistent with TPM1 expression in stem and progenitor cells, which yield both lineages. In contrast, TPM4 modifications seem limited to platelet trait variation. This indicates that TPM4 compensation may not fully account for the phenotypes seen in iPSC differentiations.

Enhanced growth in TPM1 deficient cells contrasts the detrimental effects of TPM1 deficiency in other contexts (Gieger, et al., Nature (2011) 480:201-208; Rethinasamy, et al., Circ. Res. (1998) 82:116-123; Anyanful, et al., J. Mol. Biol. (2001) 313:525-537). Most notably, *D. rerio* thrombopoiesis is essentially abrogated after treatment with tpma morpholinos (Gieger, et al., Nature (2011) 480:201-208). Since this finding more closely resembles TPM4 deficiency (Pleines, et al., J. Clin. Invest. (2017) 127:814-829), these prior results may demonstrate off-target effects or differing roles for Tpm genes in *D. rerio*. Indeed, there are significant discrepancies between zebrafish and human hematopoietic systems (Pishesha, et al., Proc. Natl. Acad. Sci. (2014) 111:4103-8).

Recent advances increasing pre-megakaryocyte platelet yields have focused a spotlight on increasing cost effectiveness of in vitro megakaryocyte generation. The results presented here indicate that TPM1 manipulation can be used to increase in vitro yield of clinically transfusable platelets. For clinical utility, it is important that TPM1-deficient megakaryocytes and platelets function normally. However, there is almost no TPM1 protein in megakaryocytes or platelets (FIG. 4D; Pleines, et al., J. Clin. Invest. (2017) 127:814-829). Further, the healthy donors sampled for GWAS had no clinically apparent bleeding disorders.

In conclusion, a penalized regression modeling and cell-based biochemical inquiry was used to define a role for TPM1 in genetically constraining megakaryocyte differentiation. The approach improves understanding of genes and mechanisms related to quantitative platelet trait variation. TPM1 manipulation improves in vitro megakaryocyte yield and help understand or treat heritable thrombocytopenia.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for producing megakaryocytes, said method comprising contacting stem cells with a tropomyosin 1 (TPM1) inhibitor and/or inactivating the TPM1 gene, thereby producing megakaryocytes,
   wherein said TPM1 inhibitor is an inhibitory nucleic acid molecule selected from the group consisting of antisense, siRNA, and shRNA; and
   wherein said inactivation of the TPM1 gene comprises delivering a gene editing system specific for the TPM1 gene to the cell.

2. The method of claim 1, wherein said stem cells are induced pluripotent stem cells.

3. The method of claim 1, further comprising contacting the stem cells with a megakaryocyte differentiation inducer.

4. The method of claim 3, wherein said megakaryocyte differentiation inducer is selected from the group consisting of vascular endothelial growth factor (VEGF), stem cell factor (SCF), thrombopoietin (TPO), and interleukin-3 (IL-3).

5. The method of claim 1, wherein said inhibitory nucleic acid molecule is siRNA.

6. The method of claim 1, wherein said gene editing system is CRISPR.

7. The method of claim 1, further comprising isolating the produced megakaryocytes.

8. The method of claim 1, further comprising activating the megakaryocytes to produce platelets.

9. The method of claim 8, wherein said megakaryocytes are contacted with thrombin, convulxin, and/or adenosine diphosphate to activate production of platelets.

10. The method of claim 8, wherein said megakaryocytes are incubated in a platelet bioreactor to activate production of platelets.

11. The method of claim 8, further comprising isolating the produced platelets.

12. A method of treating thrombocytopenia in a subject in need thereof, said method comprising administering megakaryocytes to the subject, wherein the megakaryocytes are produced by inactivating the tropomyosin 1 (TPM1) gene.

* * * * *

SEQUENCE LISTING

```
<160> NUMBER OF SEQ ID NOS: 9

<210> SEQ ID NO 1
<211> LENGTH: 284
<212> TYPE: PRT
<213> ORGANISM: Homo sapiens

<400> SEQUENCE: 1

Met Asp Ala Ile Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
                20                  25                  30

Glu Asp Arg Ser Lys Gln Leu Glu Asp Glu Leu Val Ser Leu Gln Lys
            35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Lys Cys Ala Glu
            180                 185                 190

Leu Glu Glu Glu Leu Lys Thr Val Thr Asn Asn Leu Lys Ser Leu Glu
        195                 200                 205

Ala Gln Ala Glu Lys Tyr Ser Gln Lys Glu Asp Arg Tyr Glu Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Asp Glu Leu Tyr Ala Gln Lys Leu Lys Tyr Lys Ala Ile Ser Glu
            260                 265                 270
```

```
Glu Leu Asp His Ala Leu Asn Asp Met Thr Ser Ile
        275                 280
```

```
<210> SEQ ID NO 2
<211> LENGTH: 855
<212> TYPE: DNA
<213> ORGANISM: Homo sapiens

<400> SEQUENCE: 2
atggacgcca tcaagaagaa gatgcagatg ctgaagctcg acaaggagaa cgccttggat      60
cgagctgagc aggcggaggc cgacaagaag gcggcggaag acaggagcaa gcagctggaa     120
gatgagctgg tgtcactgca aagaaactc aagggcaccg aagatgaact ggacaaatac     180
tctgaggctc tcaaagatgc ccaggagaag ctggagctgg cagagaaaaa ggccaccgat     240
gctgaagccg acgtagcttc tctgaacaga cgcatccagc tggttgagga agagttggat     300
cgtgcccagg agcgtctggc aacagctttg cagaagctgg aggaagctga aaggcagca     360 gatgagagtg agagaggcat gaaagtcatt gagagtcgag cccaaaaaga tgaagaaaaa     420
atggaaattc aggagatcca actgaaagag gccaagcaca ttgctgaaga tgccgaccgc     480
aaatatgaag aggtggcccg taagctggtc atcattgaga gcgacctgga acgtgcagag     540
gagcgggctg agctctcaga aggcaaatgt gccgagcttg aagaagaatt gaaaactgtg     600
acgaacaact tgaagtcact ggaggctcag gctgagaagt actcgcagaa ggaagacaga     660
tatgaggaag agatcaaggt cctttccgac aagctgaagg aggctgagac tcgggctgag     720
tttgcggaga ggtcagtaac taaattggag aaaagcattg atgacttaga agacgagctg     780
tacgctcaga aactgaagta caaagccatc agcgaggagc tggaccacgc tctcaacgat     840
atgacttcca tataa                                                      855
```

```
<210> SEQ ID NO 3
<211> LENGTH: 80
<212> TYPE: RNA
<213> ORGANISM: Artificial Sequence
<220> FEATURE:
<223> OTHER INFORMATION: gRNA scaffold

<400> SEQUENCE: 3
guuuuagagc uagaaauagc aaguuaaaau aaggcuaguc cguuaucaac uugaaaaagu      60
ggcaccgagu cggugcuuuu                                                  80
```

```
<210> SEQ ID NO 4
<211> LENGTH: 23
<212> TYPE: DNA
<213> ORGANISM: Artificial Sequence
<220> FEATURE:
<223> OTHER INFORMATION: guide sequence

<400> SEQUENCE: 4
atgacgaaag gtaccacgtc agg                                              23
```

```
<210> SEQ ID NO 5
<211> LENGTH: 23
<212> TYPE: DNA
<213> ORGANISM: Artificial Sequence
<220> FEATURE:
<223> OTHER INFORMATION: guide sequence

<400> SEQUENCE: 5
tgagtactga tgaaactatc agg                                              23
```

```
<210> SEQ ID NO 6
<211> LENGTH: 23
<212> TYPE: DNA
<213> ORGANISM: Artificial Sequence
<220> FEATURE:
<223> OTHER INFORMATION: guide sequence

<400> SEQUENCE: 6 ccctttctt gctgctgtgt tgg                                              23

<210> SEQ ID NO 7
<211> LENGTH: 23
<212> TYPE: DNA
<213> ORGANISM: Artificial Sequence
<220> FEATURE:
<223> OTHER INFORMATION: guide sequence

<400> SEQUENCE: 7
ggagagtgat caagaaatgg agg                                             23

<210> SEQ ID NO 8
<211> LENGTH: 11
<212> TYPE: DNA
<213> ORGANISM: Artificial Sequence
<220> FEATURE:
<223> OTHER INFORMATION: rs342293 SNP sequence

<400> SEQUENCE: 8
attatcttga g                                                          11

<210> SEQ ID NO 9
<211> LENGTH: 10
<212> TYPE: DNA
<213> ORGANISM: Artificial Sequence
<220> FEATURE:
<223> OTHER INFORMATION: rs11071720 SNP sequence

<400> SEQUENCE: 9
taataggcaa                                                            10
```